United States Patent [19]
Western et al.

[11] Patent Number: 5,612,199
[45] Date of Patent: Mar. 18, 1997

[54] METHOD FOR PRODUCING A POLYNUCLEOTIDE FOR USE IN SINGLE PRIMER AMPLIFICATION

[75] Inventors: Linda M. Western, San Mateo; Karen M. Hahnenberger, Cupertino; Samuel Rose, Mountain View; Martin Becker, Palo Alto; Edwin F. Ullman, Atherton, all of Calif.

[73] Assignee: Behringwerke AG, Marburg, Germany

[21] Appl. No.: 221,662

[22] Filed: Apr. 1, 1994

Related U.S. Application Data

[63] Continuation of Ser. No. 776,538, Oct. 11, 1991, abandoned.

[51] Int. Cl.⁶ ................................................. C12P 19/34
[52] U.S. Cl. ........................... 435/91.1; 435/91.2; 935/77; 935/78
[58] Field of Search ................................ 435/91.2, 91.1

[56] References Cited

U.S. PATENT DOCUMENTS

| | | | |
|---|---|---|---|
| 4,358,535 | 11/1982 | Falkow et al. | 435/5 |
| 4,423,153 | 12/1983 | Ranney et al. | 436/63 |
| 4,480,040 | 10/1984 | Owens et al. | 436/504 |
| 4,486,539 | 12/1984 | Ranki et al. | 436/504 |
| 4,490,472 | 12/1984 | Gottlieb | 436/504 |
| 4,599,303 | 7/1986 | Yabusaki et al. | 435/6 |
| 4,656,127 | 4/1987 | Mundy | 435/6 |
| 4,656,134 | 4/1987 | Ringold | 435/91 |
| 4,663,283 | 5/1987 | Kleid et al. | 435/91 |
| 4,675,283 | 6/1987 | Roninson | 435/6 |
| 4,677,054 | 6/1987 | White et al. | 435/6 |
| 4,683,194 | 7/1987 | Saiki et al. | 435/6 |
| 4,683,195 | 7/1987 | Mullis et al. | 435/6 |
| 4,683,202 | 7/1987 | Mullis | 435/91 |
| 4,724,202 | 2/1988 | Dattagupta et al. | 435/6 |
| 4,882,269 | 11/1989 | Schneider et al. | 435/6 |
| 4,908,307 | 3/1990 | Rodland et al. | 435/6 |
| 4,994,368 | 2/1991 | Goodman et al. | 435/6 |

FOREIGN PATENT DOCUMENTS

| | | |
|---|---|---|
| 904402 | 3/1986 | Belgium. |
| 0164054A1 | 12/1985 | European Pat. Off.. |
| 0173339 | 3/1986 | European Pat. Off. ................ 435/6 |
| 0185494A2 | 6/1986 | European Pat. Off.. |
| 0194545A2 | 9/1986 | European Pat. Off.. |
| 0200362A2 | 12/1986 | European Pat. Off.. |
| 0302175A2 | 2/1989 | European Pat. Off.. |
| WO89/12695 | 12/1989 | WIPO. |

OTHER PUBLICATIONS

Fromman et al., PNAS, USA 85:8998–9002 (Dec. 1988).
Kwok et al., Nature 339:237–238 (18 May 1989).
Nelson et al., PNAS, USA 86:6686–6690 (Sep. 1989).
U.S. Ser. No. 888,058 filed Jul. 22, 1986 by Adams.
U.S. Ser. No. 299,282 filed Jan. 19, 1989 by Rose et al.
U.S. Ser. No. 399,795 filed Jan. 19, 1989 by Rose et al.
U.S. Ser. No. 555,323 filed Jul. 19, 1990 by Rose et al.
U.S. Ser. No. 555,968 filed Jul. 19, 1990 by Rose et al.

(List continued on next page.)

*Primary Examiner*—Stephanie W. Zitomer
*Attorney, Agent, or Firm*—Theodore J. Leitereg

[57] ABSTRACT

A method is disclosed for extending an extender probe to produce a single stranded polydeoxynucleotide that is free of unreacted extender probe and has two segments that are non-contiguous and complementary with each other. The method comprises the steps of (1) providing in combination (a) a polynucleotide having two non-contiguous, non-complementary nucleotide sequences S1 and S2 wherein S2 is 5' of S1 and is at least ten deoxynucleotides long, (b) an extender probe comprised of two deoxynucleotide sequences, wherein the sequence at the 3'-end of the extender probe (EP1) is hybridizable with S1 and the other of the deoxynucleotide sequences (EP2) is substantially identical to S2 and (c) means for modifying the 3'-end of extender probe that does not hybridize with the polynucleotide and (2) extending the extender probe along the polynucleotide wherein extender probe not hybridized to the polynucleotide becomes modified at its 3'-end.

46 Claims, 5 Drawing Sheets

OTHER PUBLICATIONS

Saiki, et al., Science, (Dec. 20, 1985) vol. 230: pp. 1350–1354, "Enzymatic Amplification of β–Globin Genomic Sequences and Restriction Site Analysis for Diagnosis of Sickle Cell Anemia".

Langer, et al., Proc. Natl. Acad. Science USA, (Nov. 1981) vol. 78:11, pp. 6633–6637, "Enzymatic synthesis of biotin–labeled polynucleotides: Novel nucleic acid affinity probes".

Brigati, et al., Virology, (1983) vol. 126: pp. 32–50, "Detection of Viral Genomes in Cultured Cells and Paraffin–EMbedded Tissue Sections Using Biotin–Labeled Hybridization Probes".

Stoflet, et al., Science, (Jan. 1988) vol. 239, pp. 491–494, "Genomic Amplification with Transcript Sequencing".

Saiki, et al., Science, (Jan. 1988), vol. 239: pp. 487–491, "Primer–Directed Enzymatic Amplification of DNA with a Thermostable DNA Polymerase".

Bugawan, et al., Bio/Technology, (Aug. 1988) vol. 6: pp. 943–947, "The use of non–radioactive oligonucleotide probes to analyze enzymatically amplified DNA for prenatal diagnosis and foresic HLA typing".

Goldkorn, et al., Nucleic Acids Research, (1986) vol. 14:22, pp. 9171–9191, "A simple and efficient enzymatic method for covalent attachment of DNA to cellulose. Application for hybridization–restriction analysis and for in vitro synthesis of DNA probes".

Bischofberger, et al., Nucleic Acids Research, (1987), vol. 15:2, pp. 709–716, "Cleavage of single stranded oligonucleotides by *Eco*RI restriction endonuclease".

Lizardi, et al., Bio/Technology, (Oct. 1988) vol. 6: pp. 1197–1202, "Exponential Amplification of Recombinant–RNA Hybridization Probes".

Fahrlander, et al., Bio/Technology, (Oct. 1988) vol. 6: pp. 1165–1168, "Amplifying DNA Probe Signals: A 'Christmas Tree' Approach".

Skerra, Nucleic Acids Research, (Jul. 25, 1992) vol. 20:14, pp. 3551–3554, "Phosphorothioate primers improve the amplification of DNA sequences by DNA polymerases with proofreading activity".

Lundberg, et al., Gene, (1991) vol. 108, pp. 1–6, "High–fidelity amplification using a thermostable DNA polymerase isolated from *Pyrococcus furiosus*".

Bloch, Biochemistry, (Mar. 19, 1991) vol. 30:11, pp. 1735–2747, "A Biochemical Perspective of the Polymerase Chain Reaction".

METHOD FOR PRODUCING A POLYNUCLEOTIDE FOR USE IN SINGLE PRIMER AMPLIFICATION

This is a continuation of application U.S. Ser. No. 07/776,538, filed Oct. 11, 1991, now abandoned.

BACKGROUND OF THE INVENTION

1. Field of the Invention

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labelling of DNA with T4 kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

Current methods for detecting specific nucleic acid sequences generally involve immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about two to forty-eight hours. After the above time period, the solid support is washed several times at a controlled temperature to remove unhybridized probe. The support is then dried and the hybridized material is detected by autoradiography or by spectrometric methods.

When very low concentrations must be detected, the current methods are slow and labor intensive, and nonisotopic labels that are less readily detected than radiolabels are frequently not suitable. A method for increasing the sensitivity to permit the use of simple, rapid, nonisotopic, homogeneous or heterogeneous methods for detecting nucleic acid sequences is therefore desirable.

Recently, a method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the 5' ends of the oligonucleotide primers.

2. Description of the Prior Art

A process for amplifying, detecting and/or cloning nucleic acid sequences is disclosed in U.S. Pat. Nos. 4,683,195 and 4,683,202. Sequence polymerization by polymerase chain reaction is described by Saiki, et al., (1986) *Science,* 230:1350–1354. A method of making an oligonucleotide is described in European Patent Application No. 0194545 A2. Belgian Patent Application No. BE 904402 discloses a mold for making DNA detection probes. Gene amplification in eukaryotic cells is disclosed in U.S. Pat. No. 4,656,134.

Langer, et al., *Proc. Natl. Acad. Sci. USA,* (1981) 78:6633–6637 discloses the enzymatic synthesis of biotin labelled polynucleotides and the use of these materials as novel nucleic acid affinity probes. The detection of viral genomes in cultured cells and paraffin imbedded tissue sections using biotin labelled hybridization probes is discussed by Brigati, et al., Virology, (1983) 126:32–50. U.S. Pat. No. 4,486,539 discloses the detection of microbial nucleic acids by a one step sandwich hybridization test. Sensitive tests for malignancies based on DNA detection is described in U.S. Pat. No. 4,490,472. U.S. Pat. No. 4,480,040 discloses the sensitive and rapid diagnosis of plant viroid diseases and viruses employing radioactively labelled DNA that is complementary to the viroid or to the nucleic acid of the virus being diagnosed. European Patent Application 83106112.2 (Priority U.S. patent application 391,440 filed Jun. 23, 1982) teaches modified labelled nucleotides and polynucleotides and methods of preparing, utilizing, and detecting the same. Methods and compositions for the detection and determination of cellular DNA are disclosed in U.S. Pat. No. 4,423,153. Specific DNA probes in diagnostic microbiology are discussed in U.S. Pat. No. 4,358,535. A method for detection of polymorphic restriction sites and nucleic acid sequences is discussed in European Patent Application No. 0164054 A1. U.S. Pat. No. 4,663,283 describes a method of altering double-stranded DNA.

Genomic amplification with transcript sequencing is discussed by Stoflet, et al., *Science* (198) 239:491. Primer-directed enzymatic amplification of DNA with a thermostable DNA polymerase is described by Saiki, et al., *Science* (1988) 239:487. U.S. Pat. No. 4,724,202 discloses the use of non-hybridizable nucleic acids for the detection of nucleic acid hybridization. Bugawan, et al., describe the use of non-radioactive oligonucleotide probes to analyze enzymatically amplified DNA for prenatal diagnosis and forensic HLA typing.

Detection and isolation of homologous, repeated and amplified nucleic acid sequences is disclosed in U.S. Pat. No. 4,675,283. A single stranded self-hybridizing nucleic acid probe capable of repeatedly hybridizing to itself or other nucleic acids to form an amplified entity is described in U.S. Patent Application Ser. No. 888,058, filed Jul. 22, 1986. U.S. Pat. Nos. 4,683,195 and 4,683,202 disclose a homogeneous polynucleotide displacement assay with digestion of the displaced RNA single strand polynucleotide from the reagent complex and amplifying nucleic acid sequences with treatment of separate complementary strands of the nucleic acid with two oligonucleotide primers. European Patent Application No. 0200362 describes a process for amplifying, detecting or cloning nucleic acid sequences and useful in disease diagnosis and in preparation of transformation vectors. A method for simple analysis of relative nucleic acid levels in multiple small samples by cytoplasmic dot hybridization is described in U.S. Pat. No. 4,677,054. A hybridization method of detecting nucleic acid sequences with a probe containing a thionucleotide is described in U.S. Pat. No. 4,647,529.

A simple and efficient enzymatic method for covalent attachment of DNA to cellulose and its application for hybridization-restriction analysis and for in vitro synthesis of DNA probes is described in *Nucleic Acids Research* (1986) 14:9171–9191. Cleavage of single stranded oligonucleotides by Eco RI restriction endonuclease is described in *Nucleic Acid Research* (1987) 15:709–716.

Exponential Amplification of Recombinant-RNA Hybridization Probes is described by Lizardi, et al. (1988) *Bio/Technology* 6:1197–1202. Fahrlander, et al., discusses Amplifying DNA Probe Signals: A Christmas Tree Approach in Bio/Technology (1988) 6:1165–1168.

A nucleic acid hybridization assay employing probes cross-linkable to target sequences is described in U.S. Pat. No. 4,599,303. The method involves the preparation of a specific single stranded ribonucleic acid or deoxyribonucleic acid molecule into which a bifunctional cross-linking molecule has been covalently incorporated. The incorporation is such that the cross-linking molecule retains the capacity to undergo a second reaction with the nucleic acid of the bacterial, viral, or mammalian chromosome, which is the target for the probe such as to form a covalent cross link. Following cross-linking, the uncrossed link probe is separated from covalently cross-linked probe-target complex using one of several procedures which differentiate between single stranded probe and double stranded covalently linked probe-target complex.

A hybridization method and probe for detecting nucleic acid sequences is described in U.S. Pat. No. 4,908,307. An amplified hybridization assay is described in U.S. Pat. No. 4,882,269 wherein a family of signal-generating secondary probes bind to a primary probe that hybridizes to the target sequence of interest.

Detection of target sequences in nucleic acids by hybridization using diagnostic and contiguous probes for diagnosis of genetic abnormality diseases, especially in an automated procedure, is described in European Patent Application No. 0 185 494A2. In the method a sample is hybridized with a probe complementary to a diagnostic portion of the target sequence (the diagnostic probe) and with a probe complementary to a nucleotide sequence contiguous with the diagnostic portion (the contiguous probe) under conditions wherein the diagnostic probe remains bound substantially only to the sample nucleic acid containing the target sequence. The diagnostic probe and contiguous probe are then covalently attached to yield a target probe that is complementary to the target sequence and the probes which are not attached are removed. In a preferred mode, one of the probes is labeled so that the presence or absence of the target sequence can then be tested by melting the sample nucleic acid target probe duplex, eluting the dissociated target probe, and testing for the label.

The above method suffers at least one disadvantage in that contiguous sequences are required. To carry out the method, one must identify the diagnostic sequence and the contiguous sequence and create diagnostic and contiguous probes complementary to the above sequences. If the diagnostic and contiguous sequences are not identified precisely, then the diagnostic and contiguous probes may not hybridize sufficiently and the assay specificity and sensitivity can be lost or substantially decreased.

A DNA amplification and subtraction technique is described in WO89/12695. The method involves isolating genomic or RNA-derived duplex fragments which are unique to one of two fragment mixtures. The fragments in positive-source and negative-source mixtures are separately equipped with end linkers, and each mixture is amplified by successive primed-strand replications, using a single primer which is homologous to the associated linker. The second source linker is biotinylated, and the fragments in this mixture are hybridized in molar excess with the fragments in the positive source mixture. DNA species which are not hybridized with the biotinylated species, i.e., species that are unique to the positive source mixture, are isolated after removal of hybridized species by affinity chromatography. Also disclosed is a method of amplifying a mixture of DNA fragments by repeated linker/primer replication.

U.S. patent applications Ser. Nos. 07/299,282 filed Jan. 19, 1989, now U.S. Pat. No. 5,508,178 and 07/399,795, filed Aug. 29, 1989, respectively, describe nucleic acid amplification using a single polynucleotide primer. U.S. patent applications Ser. No. 07/555,323 filed Jul. 19, 1990, discloses methods for producing a polynucleotide for use in single primer amplification. U.S. patent application Ser. No. 07/555,968 filed Jul. 19, 1990, now U.S. Pat. No. 5,439,998 describes a method for producing a molecule containing an intramolecular base-pair structure. The disclosures of these four applications are incorporated herein by reference.

SUMMARY OF THE INVENTION

In one embodiment of the present invention a method is described for forming from an extender probe and a single stranded target polynucleotide sequence a single stranded polynucleotide sequence, which is free of unmodified extender probe, having a sequence identical to the target polynucleotide sequence attached at its 3'-end to a polynucleotide sequence complementary to a polynucleotide sequence at the 5'-end of the single stranded target polynucleotide sequence. The method comprises: (a) hybridizing to the 3'-end of the single stranded target polynucleotide sequence the 3'-end of the extender probe wherein the extender probe contains a sequence substantially identical to a sequence S2 at the 5'-end of the target polynucleotide sequence, (b) extending the extender probe along the single stranded target polynucleotide sequence, and (c) modifying the 3'-end of the extender probe not hybridized to the single stranded target polynucleotide sequence, (2) hybridizing a primer to the 3'-end of the extended extender probe, the primer having sequence S2 at its 3'-end and (e) extending the primer along the extended extender probe.

The invention disclosed herein includes methods and reagents for extending an extender probe to form a single stranded polydeoxynucleotide having two segments that are non-contiguous and complementary with each other wherein extender probe not involved in such extension is modified at its 3'-end. The method finds particular application, for example, in single primer amplification assays.

In one embodiment of the invention an extender probe is extended to produce a single stranded polydeoxynucleotide having two segments that are non-contiguous and complementary with each other. The method of production comprises the steps of (1) providing in combination (a) a polynucleotide having two non-contiguous, non-complementary nucleotide sequences, S1 and S2, wherein S2 is 5' of S1 and is at least ten nucleotides long, (b) an extender probe comprised of two deoxynucleotide sequences, wherein the sequence at the 3' end of the extender probe (EP1) is hybridizable with S1 and the other of the deoxynucleotide sequences (EP2) is substantially identical to S2 and (c) means for modifying the 3'-end of the extender probe that does not hybridize with the polynucleotide and (d) extending the extender probe along the polynucleotide wherein extender probe not hybridized to the polynucleotide becomes modified at its 3'-end.

In the above embodiment of the present invention a polydeoxynucleotide primer capable of hybridizing at least at its 3'-end with a nucleotide sequence complementary to S2, DNA polymerase, and deoxynucleoside triphosphates are provided in the combination under conditions where (a) the extender probe is extended along the polynucleotide to form a duplex, (b) the 3'-end of the extender probe not hybridized with the polynucleotide is modified, (c) the extended extender probe is dissociated from the duplex, (d) the polydeoxynucleotide primer hybridizes with and is extended along the extended extender probe to form a second duplex comprising extended primer, (e) the extended primer is dissociated from the second duplex, and (f) the primer hybridizes with and is extended along the extended primer to form a duplex comprising extended primer, and steps (e) and (f) are repeated.

Another embodiment of the invention is a method for forming a single stranded polynucleotide sequence complementary to a single stranded target polynucleotide sequence. The method comprises: (a) combining in a medium the single stranded target polynucleotide sequence, a DNA polymerase with 3' exonuclease activity, and an extender probe comprised of a sequence complementary to a sequence at the 3'-end of the single stranded target polynucleotide sequence wherein the complementary extender probe sequence contains at least one thiophosphate and does not terminate at the 3' terminus of the extender probe, and (b) treating the medium to cause hybridization of the extender probe to the single stranded target polynucleotide sequence, extension of the extender probe along the single stranded target polynucleotide sequence, and degradation of the 3' terminus of the extender probe.

In another embodiment the presence of a target polynucleotide sequence in a medium suspected of containing the target polynucleotide sequence is detected. The target polynucleotide sequence has two non-contiguous, non-hybridizable nucleotide sequences, S1 and S2, wherein S2 is 5' of S1 and at least 10 nucleotides long. The method comprises the steps of:

(a) providing in combination, either concomitantly or wholly or partially sequentially, (1) the medium, (2) an extender probe having two deoxynucleotide sequences wherein the sequence at the 3'-end of the extender probe (EP1) is hybridizable with S1 and the other of the deoxynucleotide sequences (EP2) is substantially identical to S2, (3) means for modifying the 3'-end of the extender probe not hybridized with the target polynucleotide sequence, (4) a polydeoxynucleotide primer capable of hybridizing with a nucleotide sequence complementary to S2 with the proviso that the primer may be generated in situ, (5) DNA polymerase and (6) deoxynucleoside triphosphates under conditions wherein (A) extender probe hybridizes with and is extended along (extended EP) the target polynucleotide sequence to form a duplex, (B) extender probe not hybridized to the target polynucleotide sequence is modified at its 3'-end, (C) the extended EP is dissociated from the duplex, (D) the primer hybridizes with and is extended along the extended EP to form a second duplex comprising extended primer, (E) the extended primer is dissociated from the duplex, and (F) the primer hybridizes with and is extended along the extended primer to form a duplex comprising extended primer and steps (E) and (F) are repeated, and (b) examining for the presence of the extended primer.

Another embodiment of the invention involves a method for detecting the presence of a polynucleotide analyte in a sample suspected of containing the polynucleotide analyte. The method comprises the steps of:

(a) treating a medium containing the sample to form a single stranded target polynucleotide sequence from the polynucleotide analyte, if present, the target polynucleotide sequence having two non-contiguous, non-complementary nucleotide sequences, S1 and S2, wherein S2 is 5' of S1, and is at least ten nucleotides long, (b) combining the medium with (1) an extender probe having two polydeoxynucleotide sequences wherein the sequence at the 3'-end of the extender probe (EP1) is hybridizable with S1 and the other of the deoxynucleotide sequence (EP2) is substantially identical to S2, (2) a nucleotide sequence (NS) having a portion capable of hybridizing with EP1 wherein NS may be a separate molecule or part of the extender probe, (3) a polydeoxynucleotide primer capable of hybridizing with a nucleotide sequence complementary to S2 when means for degrading said extender probe to form said polydeoxynucleotide primer is not present, (4) deoxynucleoside triphosphates, and (5) DNA template dependent polydeoxynucleotide polymerase under conditions wherein (A) extender probe is hybridized with and is extended along (extended extender probe) the target polynucleotide sequence to form a duplex, (B) extender probe not hybridized to the target polynucleotide sequence is extended along NS, (C) the extended extender probe is dissociated from the duplex, (D) the primer hybridizes with and is extended along the extended extender probe to form a duplex comprising extended primer, (E) the extended primer is dissociated from the duplex, and (F) the primer hybridizes with and is extended along the extended primer to form a duplex comprising extended primer, and steps (E) and (F) are repeated, wherein steps (a) and (b) are performed concomitantly or wholly or partially sequentially, and (c) examining for the presence of the extended primer.

Another embodiment of the invention concerns a method for detecting the presence of a polynucleotide analyte in a sample suspected of containing the polynucleotide analyte. The method comprises the steps of:

(a) treating a medium containing the sample to form a single stranded target polynucleotide sequence from the polynucleotide analyte, if present, the target polynucleotide sequence having two non-contiguous, non-complementary nucleotide sequences S1 and S2 wherein S2 is 5' of S1, and is at least ten nucleotides long, (b) combining the medium with (1) an extender probe having two deoxynucleotide sequences wherein the sequence at the 3'-end of the extender probe (EP1) is hybridizable with S1 and the other of the deoxynucleotide sequences (EP2) is substantially identical to S2 and not complementary to the target polynucleotide sequence, (2) an enzyme capable of degrading single stranded polynucleotides, (3) a polydeoxynucleotide primer capable of hybridizing with a nucleotide sequence complementary to S2 when means for degrading said extender probe to form said polynucleotide primer is not present, (4) deoxynucleoside triphosphates, and (5) DNA template dependent polydeoxynucleotide polymerase under conditions wherein (A) the extender probe is hybridized with and is extended along the target polynucleotide sequence to form a duplex, (B) extender probe not hybridized to the target polynucleotide sequence is degraded, (C) the extended extender probe is dissociated from the duplex, (D) the primer hybridizes with and is extended along the extended extender probe, (E) the extended primer is dissociated from the duplex, and (F) the primer hybridizes with and is extended along the extended primer to form a duplex comprising extended primer and steps (E) and (F) are repeated, wherein steps (a) and (b) are performed concomitantly or wholly or partially sequentially, and (c) examining for the presence of the extended primer.

The invention further includes kits comprising in packaged combination (a) a polydeoxynucleotide extender probe having at its 3'-end a sequence (EP1) hybridizable with a first sequence in a target polynucleotide sequence and having a sequence (EP2) that is substantially identical to a second sequence of the target polynucleotide sequence, wherein in the target polynucleotide sequence the second sequence is 5' of, and non-contiguous with, the first sequence, (b) means for modifying the 3'-end of extender probe not hybridized with the target polynucleotide sequence, and (c) a polydeoxynucleotide primer capable of hybridizing with a sequence that is complementary with the second sequence.

DESCRIPTION OF THE SPECIFIC EMBODIMENTS

Figure 1:
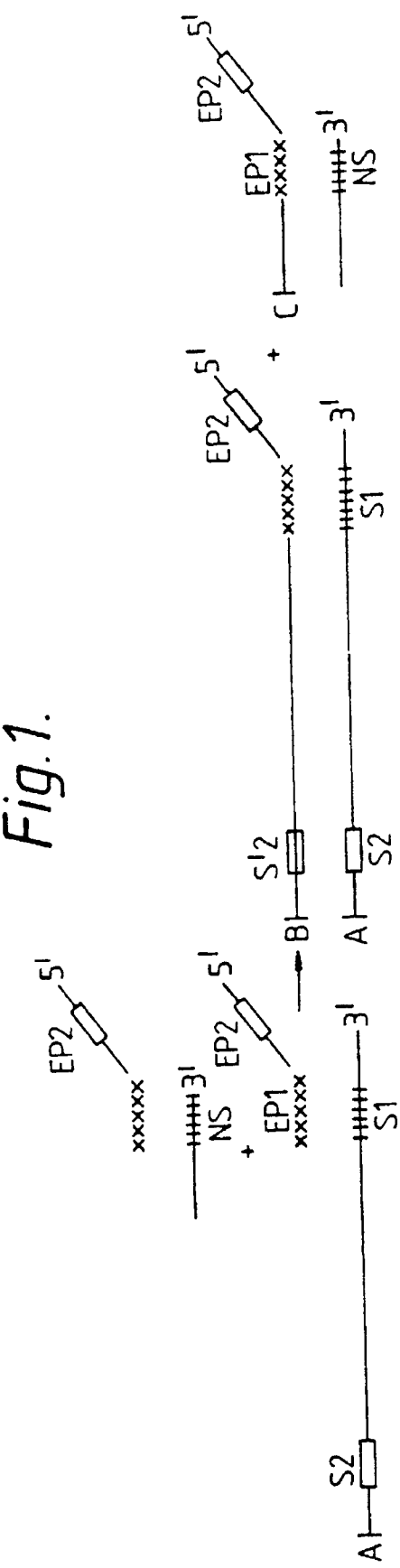
FIG. 1 is a schematic of one embodiment in accordance with the present invention.

The present method allows extension of an extender probe along single stranded (ss) target polynucleotide sequence to produce a single stranded polynucleotide having the capability of forming an intramolecularly base-paired structure wherein the 3'-end of extender probe not involved in the production of the single stranded polynucleotide is modified. The single stranded polynucleotide produced in this manner can have an intramolecularly base-paired structure, i.e., two segments that are non-contiguous and complementary with each other, sometimes referred to as an inverted repeat. The method has particular application in the area of single primer amplification described above, in which a target polynucleotide sequence in a sample is amplified when such target polynucleotide sequence has an inverted repeat or can be converted to such a structure. The present method provides a highly convenient method for converting a polynucleotide sequence of interest to a target polynucleotide sequence having an intramolecularly base-paired structure while minimizing the number of reagents and steps required.

In its broadest aspect the present invention provides for production of a single stranded polynucleotide sequence having an inverted repeat that is formed from an extender probe, wherein all the extender probe not hybridized to a target polynucleotide sequence is modified at its 3'-end and is accordingly not present in unmodified form in the medium containing the newly formed single stranded polynucleotide. A target polynucleotide sequence is combined in a medium with an extender probe comprising (1) a sequence at the 3'-end of the extender probe that is complementary to a first sequence at the 3'-end of a target polynucleotide sequence within the target polynucleotide sequence and (2) a second sequence of the extender probe that is substantially identical to a second sequence of the target polynucleotide sequence, wherein each of said second sequences is 5' of each of said first sequences. The medium is treated to cause hybridization of the extender probe to the target polynucleotide sequence, along which the extender probe is extended, and to cause degradation of the 3'-end of the extender probe not hybridized to the target polynucleotide sequence.

Before proceeding further with a description of the specific embodiments of the present invention, a number of terms will be defined.

Polynucleotide analyte—a compound or composition to be measured that is a polymeric nucleotide, which in the intact natural state can have about 20 to 500,000 or more nucleotides and in an isolated state can have about 30 to 50,000 or more nucleotides, usually about 100 to 20,000 nucleotides, more frequently 500 to 10,000 nucleotides. It is thus obvious that isolation of the analyte from the natural state often results in fragmentation. The polynucleotide analytes include nucleic acids from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide analyte can be only a minor fraction of a complex mixture such as a biological sample. The analyte can be obtained from various biological material by procedures well known in the art. Some examples of such biological material by way of illustration and not limitation are disclosed in Table I below.

TABLE I

| Microorganisms of interest include: |
| --- |
| Corynebacteria |
| *Corynebacterium diphtheria* |
| Pneumococci |
| *Diplococcus pneumoniae* |
| Streptococci |
| *Streptococcus pyrogenes* |
| *Streptococcus salivarus* |
| Staphylococci |
| *Staphylococcus aureus* |

TABLE I-continued

Microorganisms of interest include:

| | |
|---|---|
| Staphylococcus albus | |
| Neisseria | |
| | |
| Neisseria meningitidis | |
| Neisseria gonorrhea | |
| Enterobacteriaciae | |
| | |
| Escherichia coli | |
| Aerobacter aerogenes | The colliform |
| Klebsiella pneumoniae | bacteria |
| Salmonella typhosa | |
| Salmonella choleraesuis | The Salmonellae |
| Salmonella typhimurium | |
| Shigella dysenteria | |
| Shigella schmitzii | |
| Shigella arabinotarda | |
| | The Shigellae |
| Shigella flexneri | |
| Shigella boydii | |
| Shigella sonnei | |
| Other enteric bacilli | |
| | |
| Proteus vulgaris | |
| Proteus mirabilis | Proteus species |
| Proteus morgani | |
| Pseudomonas aeruginosa | |
| Alcaligenes faecalis | |
| Vibrio cholerae | |
| Hemophilus-Bordetella group | Rhizopus oryzae |
| | |
| Hemophilus influenza, H. ducryi | Rhizopus arrhizua |
| | Phycomycetes |
| Hemophilus hemophilus | Rhizopus nigricans |
| Hemophilus aegypticus | Sporotrichum schenkii |
| Hemophilus parainfluenza | Flonsecaea pedrosoi |
| Bordetella pertussis | Fonsecacea compact |
| Pasteurellae | Fonsecacea dermatidis |
| | |
| Pasteurella pestis | Cladosporium carrionii |
| Pasteurella tulareusis | Phialophora verrucosa |
| Brucellae | Aspergillus nidulans |
| | |
| Brucella melitensis | Madurella mycetomi |
| Brucella abortus | Madurella grisea |
| Brucella suis | Allescheria boydii |
| Aerobic Spore-forming Bacilli | Phialophora jeanselmei |
| | |
| Bacillus anthracis | Microsporum gypseum |
| Bacillus subtilis | Trichophyton |
| | mentagrophytes |
| Bacillus megaterium | Keratinomyces ajelloi |
| Bacillus cereus | Microsporum canis |
| Anaerobic Spore-forming Bacilli | Trichophyton rubrum |
| | |
| Clostridium botulinum | Microsporum adouini |
| Clostridium tetani | Viruses |
| | |
| Clostridium perfringens | Adenoviruses |
| Clostridium novyi | Herpes Viruses |
| | |
| Clostridium septicum | Herpes simplex |
| Clostridium histolyticum | Varicella (Chicken pox) |
| Clostridium tertium | Herpes Zoster (Shingles) |
| Clostridium bifermentans | Virus B |
| Clostridium sporogenes | Cytomegalovirus |
| Mycobacteria | Pox Viruses |
| | |
| Mycobacterium tuberculosis hominis | Variola (smallpox) |
| Mycobacterium bovis | Vaccinia |
| Mycobacterium avium | Poxvirus bovis |
| Mycobacterium leprae | Paravaccinia |
| Mycobacterium paratuberculosis | Molluscum contagiosum |
| Actinomycetes (fungus-like bacteria) | Picornaviruses |
| | |
| Actinomyces Isaeli | Poliovirus |
| Actinomyces bovis | Coxsackievirus |

TABLE I-continued

Microorganisms of interest include:

| | |
|---|---|
| Actinomyces naeslundii | Echoviruses |
| Nocardia asteroides | Rhinoviruses |
| Nocardia brasiliensis | Myxoviruses |
| | |
| The Spirochetes | Influenza(A, B, and C) |
| | |
| Treponema pallidum Spirillum minus | Parainfluenza (1–4) |
| Treponema pertenue Streptobacillus monoiliformis | Mumps Virus |
| | Newcastle Disease Virus |
| Treponema carateum | Measles Virus |
| Borrelia recurrentis | Rinderpest Virus |
| Leptospira icterohemorrhagiae | Canine Distemper Virus |
| Leptospira canicola | Respiratory Syncytial Virus |
| | |
| Trypanasomes | Rubella Virus |
| Mycoplasmas | Arboviruses |
| | |
| Mycoplasma pneumoniae | |
| Other pathogens | Eastern Equine |
| | |
| Virus | Eucephalitis |
| Listeria monocytogenes | Western Equine |
| Virus | Eucephalitis |
| Erysipelothrix rhusiopathiae | Sindbis Virus |
| Streptobacillus moniliformis | Chikugunya Virus |
| Donvania granulomatis | Semliki Forest Virus |
| Bartonella bacilliformis | Mayora Virus |
| Rickettsiae (bacteria-like parasites) | St. Louis Encephalitis Virus |
| | |
| Rickettsia prowazekii | California Encephalitis Virus |
| Rickettsia mooseri | Colorado Tick Fever Virus |
| Rickettsia rickettsii | Yellow Fever Virus |
| Rickettsia conori | Dengue Virus |
| Rickettsia australis | Reoviruses |
| | |
| Rickettsia sibiricus | Reovirus Types 1–3 |
| | Retroviruses |
| | |
| Rickettsia akari (HIV) | Human Immunodeficiency Viruses |
| Rickettsia tsutsugamushi | Human T-cell Lymphotrophic Virus I & II (HTLV) |
| Rickettsia burnetti | Hepatitis |
| | |
| Rickettsia quintana | Hepatitis A Virus |
| Chlamydia (unclassifiable parasites bacterial/viral) | Hepatitis B Virus |
| | Hepatitis nonA-nonB Virus |
| | |
| Chlamydia agents (naming uncertain) | Tumor Viruses |
| | |
| Fungi | Rauscher Leukemia Virus |
| | |
| Cryptococcus neoformans | Gross Virus |
| Blastomyces dermatidis | Maloney Leukemia Virus |
| Hisoplasma capsulatum | |
| Coccidioides immitis | Human Papilloma Virus |
| Paracoccidioides brasiliensis | |
| Candida albicans | |
| Aspergillus fumigatus | |
| Mucor corymbifer (Absidia corymbifera) | |

The polynucleotide analyte, where appropriate, may be treated to cleave the analyte to obtain a fragment that contains a target polynucleotide sequence, for example, by shearing or by treatment with a restriction endonuclease or other site specific chemical cleavage method. However, it is an advantage of the present invention that the polynucleotide analyte can be used in its isolated state without further cleavage.

For purposes of this invention, the polynucleotide analyte, or a cleaved fragment obtained from the polynucleotide analyte, will usually be at least partially denatured or single stranded or treated to render it denatured or single stranded. Such treatments are well-known in the art and include, for instance, heat or alkali treatment. For example, double stranded DNA can be heated at 90–°100° C. for a period of about 1 to 10 minutes to produce denatured material.

Target polynucleotide sequence—a sequence of nucleotides to be identified, usually existing within a polynucleotide analyte, the identity of which is known to an extent sufficient to allow preparation of an extender probe polydeoxynucleotide that will hybridize with at least a portion of such target sequence, usually at least a ten nucleotide segment at the 3'-end thereof and preferably at least 15, frequently 20 to 50 nucleotide segment thereof and that comprises at least a ten nucleotide segment substantially identical to the 5'-end thereof. The target polynucleotide sequence has two non-contiguous, non-complementary nucleotide sequences, S1 and S2, one of which (S1) is the aforesaid portion capable of hybridizing to an extender probe polydeoxynucleotide wherein S2 is 5' of S1. The target polynucleotide sequence usually will contain from about 30 to 5,000 or more nucleotides, preferably 50 to 1,000 nucleotides. The two non-contiguous, non-complementary nucleotide sequences, S1 and S2, preferably contain from 10 to 100 nucleotides each and are separated by at least ten bases, preferably at least 100, usually 200 to 10,000. One target polynucleotide sequence is frequently a part of the polynucleotide analyte. The target polynucleotide sequence will generally be a fraction of a larger molecule or it may be substantially the entire molecule. The minimum number of nucleotides in the target polynucleotide sequence will be selected to assure that the presence of target polynucleotide sequence in a sample will be a specific indicator of the presence of polynucleotide analyte in a sample. Very roughly, the sequence length will usually be greater than about 1.6 log L nucleotides where L is the number of base pairs in the genome of the biologic source of the sample. The maximum number of nucleotides in the target sequence will normally be governed by the length of the polynucleotide analyte and its tendency to be broken by shearing, or other processes during isolation and any procedures required to prepare the sample for assay and the efficiency of detection and/or amplification of the sequence.

Single stranded polydeoxynucleotide sequence—a sequence of deoxynucleotides that is formed as a result of the present invention. It will normally be comprised at least of two segments or flanking sequences that are non-contiguous and complementary with each other. It may also contain one or more sequences which, when bound to their complementary sequences, are specific binding sites for receptors such as repressors, restriction enzymes, and the like. The first and second segments or flanking sequences are at the 3'-end and 5'-end, respectively, of the single stranded polynucleotide sequence and each comprises at least ten, preferably at least 15, deoxynucleotides, and/or derivatives thereof.

The single stranded polydeoxynucleotide sequence will usually contain from 30 to 10,000 deoxynucleotides, preferably 100 to 2,000 deoxynucleotides, more preferably 500 to 5,000 deoxynucleotides. When the single stranded polydeoxynucleotide sequence is hybridized with a complementary strand, each end will have a member of a pair of inverted repeats.

Polydeoxynucleotide primer—a polydeoxynucleotide, usually a synthetic deoxynucleotide that is single stranded, containing a sequence at its 3'-end that is identical with the sequence S2 or hybridizable with a nucleotide sequence complementary with the sequence S2 of the target polynucleotide sequence. Normally the polydeoxynucleotide primer will have at least 90%, preferably 100%, of the same basic sequence as the second nucleotide sequence EP2 of the extender probe. The number of deoxynucleotides in the hybridizable sequence of polydeoxynucleotide primer should be such that stringency conditions used to hybridize the polydeoxynucleotide primer will prevent excessive random non-specific hybridization. Usually, the number of deoxynucleotides in the polydeoxynucleotide primer will be at least as great as in the S2 sequence of the target polynucleotide sequence, namely, at least ten deoxynucleotides, preferably at least 15 deoxynucleotides and generally from about 10 to 200, preferably 20 to 50, deoxynucleotides.

Deoxynucleoside triphosphates—a deoxynucleoside having a 5'-triphosphate substituent. The deoxynucleosides are pentose sugar derivatives of nitrogenous bases of either purine or pyrimidine derivation, covalently bonded to the 1'-carbon of the pentose sugar. The purine bases include adenine(A), guanine(G), inosine, and derivatives and analogs thereof. The pyrimidine bases include cytosine (C), thymine (T), uracil (U), and derivatives and analogs thereof.

The derivatives and analogs are exemplified by those that are recognized and polymerized in a similar manner to the underivitized nucleoside triphosphates. Examples of such derivatives or analogs by way of illustration and not limitation are those which are modified with a reporter group, biotinylated, amine modified, radiolabeled, alkylated, and the like and also include phosphorothioate, phosphite, ring atom modified derivatives, and the like. The reporter group can be a fluorescent group such as fluorosein, a chemiluminescent group such as luminol, a terbium chelator such as N-(hydroxyethyl) ethylenediaminetriacetic acid that is capable of detection by delayed fluorescence, and the like.

Polydeoxynucleotide polymerase—a catalyst, usually an enzyme, for forming an extension of the polydeoxynucleotide primer along a DNA template including the single stranded polydeoxynucleotide where the extension is complementary thereto. The polydeoxynucleotide polymerase is a template dependent polydeoxynucleotide polymerase and utilizes the deoxynucleoside triphosphates as building blocks for extending the 3'-end of the polydeoxynucleotide primer to provide a sequence complementary with the single stranded polydeoxynucleotide sequence. Usually, the catalysts are enzymes, such DNA polymerases such as, for example, prokaryotic DNA polymerase (I, II, or III), T4 DNA polymerase, T7 DNA polymerase, Klenow fragment, reverse transcriptase, and the like, derived from any source such as cells, bacteria, such as *E. coli*, plants, animals, virus, thermophilic bacteria, and so forth. Where the polynucleotide or target polynucleotide sequence is RNA, reverse transcriptase would be included to facilitate extension of the extender probe along the polynucleotide or target polynucleotide sequence.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of cosolvents, lowering the salt concentration, and the like.

Homologous or substantially identical—In general, two polynucleotide sequences that are identical or can each hybridize to the same polynucleotide sequence are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence.

Extender probe—is a single polynucleotide strand, usually a synthetic oligonucleotide, comprised of two sequences of nucleotides, one of such sequences (EP1) located at the 3'-end of the strand, being a deoxynucleotide sequence having preferably at least ten consecutive deoxynucleotides and capable of hybridizing with a first polynucleotide sequence (S1) of the target polynucleotide sequence.

The major criteria for choosing EP1 are: (1) The sequence should be reliable, that is, it should be closely or exactly complementary with S1 and should be of sufficient length to provide stable and specific binding. (2) The 3'-end must have, or be capable of forming, a free 3'-hydroxyl group. The minimum length of EP1 will usually be at least 10, normally at least 15, preferably 20–50, deoxynucleotides. In general, EP1 will be about 20 to 100 deoxynucleotides. The combined length of the first and second polynucleotide sequences of the extender probe is at least about 20 nucleotides, preferably about 40 to 200 nucleotides, in length.

The second polynucleotide sequence of the extender probe (EP2) is a sequence of nucleotides substantially identical or homologous to the second polynucleotide sequence (S2) of a target polynucleotide sequence. EP2 is at least 10 nucleotides, usually at least 15, preferably 20–50 deoxynucleotides, in length. In general EP2 will be about 20 to 100 deoxynucleotides.

The extender probe may contain additional receptor binding or spacer sequences or other sequences located between EP1 and EP2 or at the end of EP2.

Non-contiguous—sequences are non-contiguous, there being at least one usually at least 10 nucleotides present in the target polynucleotide sequence between the two segments or between two sequences, S1 and S2, of a polynucleotide.

Contiguous—sequences are considered to be contiguous when there are no nucleotides between two segments or between two sequences of a polynucleotide.

Copy—means a sequence that is a direct identical or homologous copy of a single stranded polynucleotide sequence as differentiated from a sequence that is complementary to the sequence of such single stranded polynucleotide. In single primer amplification conducted in conjunction with the present invention, a complementary sequence of a single stranded polydeoxynucleotide sequence is produced initially as the result of the extension of the polydeoxynucleotide primer, and a sequence that is a direct copy of the single stranded polydeoxynucleotide sequence is subsequently obtained from the aforementioned complementary sequence.

Means for extending an extender probe—an extender probe having an extendable 3'-terminus can be extended by combining the extender probe hybridized to a polynucleotide, such as a target polynucleotide sequence, with a polydeoxynucleotide polymerase and deoxynucleoside triphosphates under conditions for extending the extender probe. In this way the extender probe is extended along the polynucleotide to form a duplex. When extension occurs along the target polynucleotide sequence, the duplex is comprised of the extended extender probe. Extension in this fashion provides the requisite fidelity between the two strands so that subsequent amplification of the extended extender probe provides accurate detection of the target of interest.

Means for extending a primer—a polydeoxynucleotide primer having an extendable 3'-terminus can be extended by combining the primer hybridized to extended extender probe or extended primer with a polydeoxynucleotide polymerase and deoxynucleoside triphosphates under conditions for extending the primer. In this way the primer is extended along the extended extender probe or extended primer to form a duplex comprising the extended primer. Extension in this fashion provides the requisite fidelity between the extended primer and the polynucleotide so that accurate detection of target analytes can be achieved.

Means for modifying the 3'-end of the extender probe—for single primer amplification as described above complementary base sequences in a single polynucleotide strand capable of forming a stem loop structure or inverted repeat are utilized. Such polynucleotide is either present in a sample or is created in response to the presence of a polynucleotide analyte. An extender probe is utilized to create such a polynucleotide by virtue of binding to a target polynucleotide, along which the extender probe is extended. Since the concentration of polynucleotide analyte is generally low and unknown, there are molecules of extender probe that do not hybridize with the target polynucleotide sequence. These molecules of extender probe are undesirable because they might result in competing processes, which reduce the efficiency of single primer amplification. By employing appropriate means the 3'-end of extender probe not bound to a target polynucleotide sequence can be modified such that it can no longer be extended along the target polynucleotide sequence in the presence of deoxynucleoside triphosphates and DNA polymerase.

One way in which the 3'-end of the extender probe can be modified is by degradation. For example, an enzyme such as an 3'-exonuclease can be added to the reaction medium. Under certain conditions such an enzyme degrades the 3'-end of single stranded polynucleotides. Examples of such exonuclease enzymes, by way of illustration and not limitation, are Klenow fragment, T4 polymerase, and T7 polymerase. In one approach, the polydeoxynucleotide polymerase, such as DNA polymerase, utilized for the extension of the extender probe has exonuclease activity. Exemplary of such DNA polymerases are Klenow, T4 and T7 DNA polymerases.

In another embodiment the 3'-end of the extender probe is extended along a scavenger polynucleotide that has a sequence NS at other than its 5'-end, said sequence being hybridizable with the 3'-end of the extender probe. When the 3'-terminus of the extender probe and the scavenger polynucleotide sequence are hybridized, the 3'-end of the extender probe can be extended along the scavenger polynucleotide sequence in the presence of polydeoxynucleotide polymerase and deoxynucleoside triphosphates. This process results in modification of the 3'-end of the extender probe, thereby rendering the extender probe incapable of extension along the target polynucleotide sequence or its complement during single primer amplification. The scavenger polynucleotide sequence is, generally, 8 to 1,000 or more nucleotides, preferably 10 to 50 nucleotides, in length and may be part of the extender probe or a molecule separate from the extender probe. When the scavenger polynucleotide sequence is part of the extender probe, it may be 3' or 5' of the sequence EP2 of the extender probe. Enzymes that can be utilized in this chain extension are commercially available thermophilic nucleotide polymerases such as, by way of example and not limitation, Taq, Vent, Hot Tub and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component C1q, DNA binding proteins or ligands and the like.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to the support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

Label or reporter group or reporter molecule—a member of the signal producing system. Usually the label or reporter group or molecule is conjugated to or becomes bound to a polynucleotide probe or a polydeoxynucleotide primer and is capable of being detected directly or, through a specific binding reaction, and can produce a detectable signal. Labels include a polynucleotide primer or specific polynucleotide sequence that can provide a template for amplification or ligation or act as a ligand such as for a repressor protein. Preferably, the polydeoxynucleotide primer will have, or be capable of having, a label. In general, any label that is detectable can be used. The label can be isotopic or nonisotopic, usually non-isotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence.

Signal Producing System—The signal producing system may have one or more components, at least one component being the label or reporter group. The signal producing system generates a signal that relates to the presence or amount of target polynucleotide sequence or a polynucleotide analyte in a sample. The signal producing system includes all of the reagents required to produce a measurable signal. When the label is not conjugated to a nucleotide sequence, the label is normally bound to an sbp member complementary to an sbp member that is bound to or part of a nucleotide sequence. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. The signal-producing system is described more fully in U.S. patent application Ser. No. 07/555,968, filed Jul. 19, 1990, now U.S. Pat. No. 5,439,998 the relevant disclosure of which is incorporated herein by reference.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

In one aspect of the invention a method is provided for forming a single stranded polynucleotide sequence complementary to a single stranded target polynucleotide sequence wherein an extender probe is extended along the target and extender probe not hybridized to the target polynucleotide sequence is modified at its 3'-end.

One embodiment of the method is depicted schematically in FIG. 1. EP1, located at the 3'-end of the extender probe, hybridizes with S1 of the target polynucleotide sequence and with a portion of a scavenger polynucleotide containing sequence NS. EP2 is homologous with S2. The extender probe is extended along A to produce an extended extender probe B containing sequence S'2, which is complementary to S2. B now contains EP2 and S'2, which are hybridizable with each other. Extender probe not hybridized with the target polynucleotide sequence hybridizes with NS and is extended along the scavenger polynucleotide to produce a modified extender probe C, wherein EP1 is no longer located at a 3'-end. Preferably, NS is about 8 to 100, more preferably 8 to 30, nucleotides in length.

Figure 2:
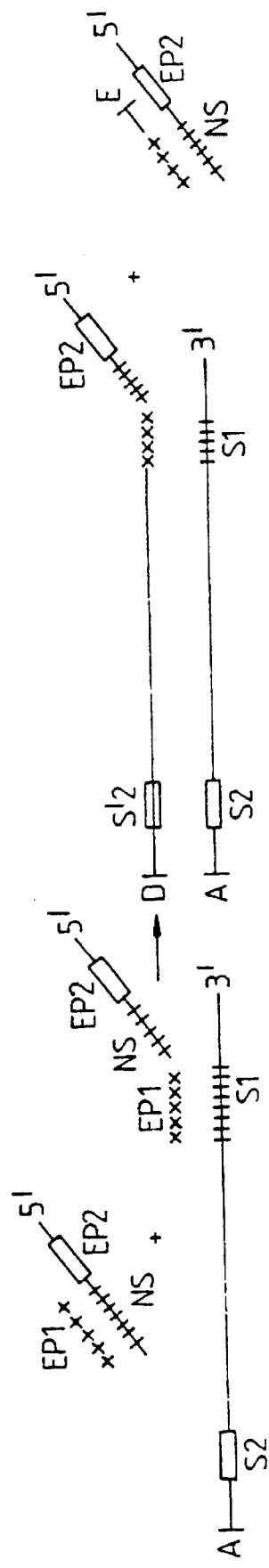
FIG. 2 is a schematic of another embodiment in accordance with the present invention.

Another embodiment of the invention is depicted in FIG. 2. In this embodiment the extender probe contains not only EP1 and EP2, but also contains the sequence NS, which is 3' of sequence EP2. NS is homologous to S1. EP1, located at the 3'-end of the extender probe, hybridizes with S1 of the target polynucleotide sequence and with NS of the extender probe. EP2 is homologous with S2. The extender probe is extended along A to produce an extended extender probe D containing a sequence S'2, which is complementary to S2. D now contains EP2 and S'2, which are hybridizable with each other. Extender probe not hybridized with the target polynucleotide sequence loops back on and hybridizes with itself, EP1 hybridizing with NS. The 3'-end of this extender probe is extended along itself to produce a modified extender probe E, wherein EP1 is no longer located at a 3'-end.

Figure 3:
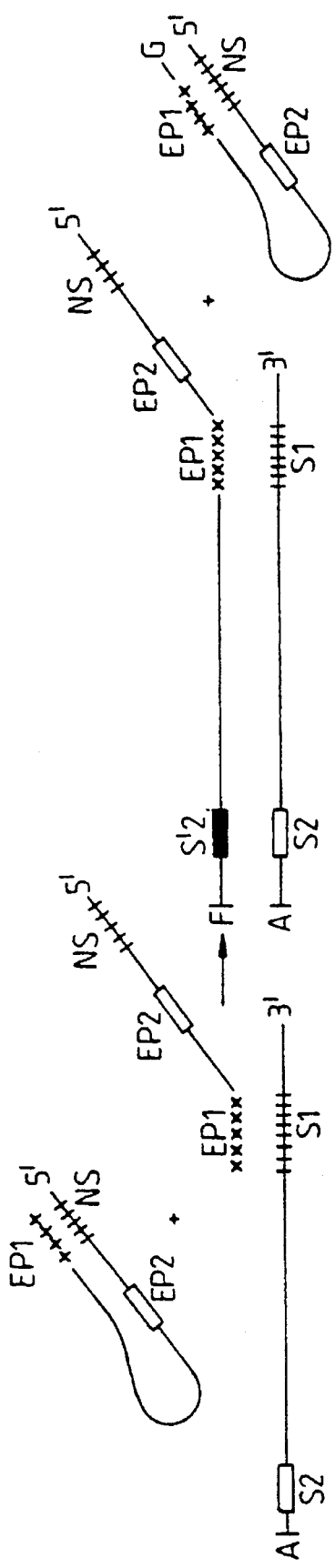
FIG. 3 is a schematic of another embodiment in accordance with the present invention.

Another alternate embodiment is shown in FIG. 3, the sequence NS is contained in the extender probe 5' of EP2. Hybridization and extension of the extender probe with the target polynucleotide sequence and with itself take place as described above for the embodiment of FIG. 2.

Figure 4:
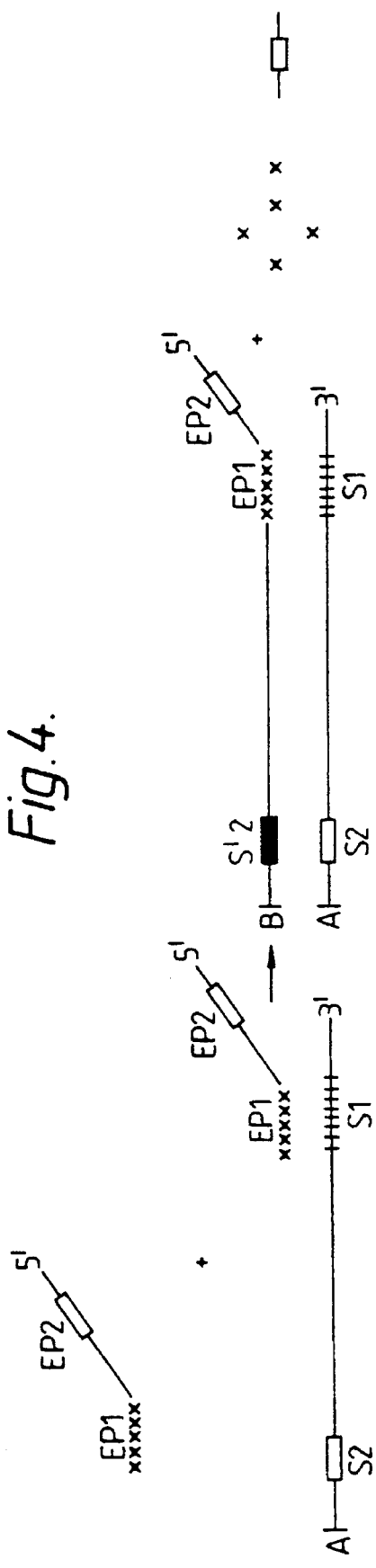
FIG. 4 is a schematic of another embodiment in accordance with the present invention.
Figure 5:
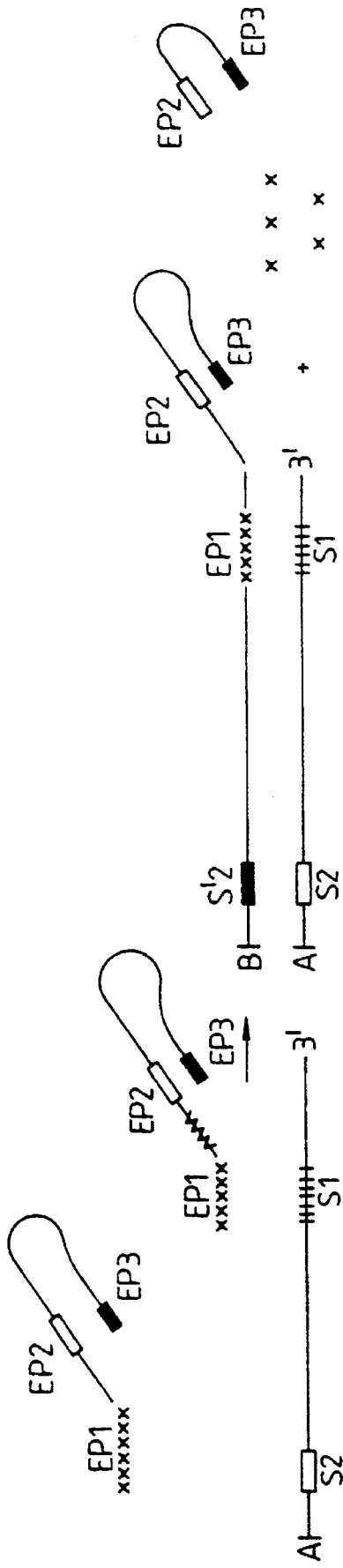
FIG. 5 is a schematic of another embodiment in accordance with the present invention.

In another alternative embodiment of the present invention as depicted in FIG. 4, EP1 of the extender probe hybridizes with S1 of the target polynucleotide sequence. The extender probe is extended along A to produce extended extender probe B as described above for the embodiment of FIG. 1. Present in the reaction mixture is an exonuclease having 3' activity, which degrades extender probe not hybridized with A to an extent sufficient to destroy its ability to hybridize at its 3'-end with S1. A variation of the embodiment of FIG. 4 is shown in FIG. 5. The extender probe contains not only EP1 and EP2 but also contains EP3, which is a sequence capable of hybridizing with EP2 and is preferably complementary with at least the 3'-end of EP2. EP1 of the extender probe hybridizes with S1 of the target polynucleotide sequence. Extended extender probe B is formed as described above for the embodiment of FIG. 4. The exonuclease degrades extender probe not bound to the target polynucleotide sequence back to its double strand formed by the hybridization of EP3 and EP2. The extender probe, in this embodiment, is designed such that its degradation removes at least EP1. Preferably, EP2 is about 5 to 50, more preferably, 8 to 30, nucleotides in length. The variant provides the option to use the degraded extender probe as a primer in a subsequent step in which EP2 of the degraded extender probe binds to S2 of the extended extender probe and extends along the extended extender probe.

The methods find use in single primer amplification wherein one or more copies of a target polynucleotide sequence, i.e., sequences identical to the target polynucleotide sequence, are formed free of any extender probe. Extender probe is hybridized to a target polynucleotide sequence and is extended as described above. Extender probe not bound to the target is modified at its 3'-end in any of the embodiments mentioned above. A polydeoxynucleotide primer is then hybridized at least at its 3'-end with a nucleotide sequence complementary to S2 under conditions where (1) the extended extender probe is rendered single stranded, (2) the polydeoxynucleotide primer hybridizes with and is extended along the extended extender probe to form a duplex comprising extended primer, which contains a sequence identical to the target polynucleotide sequence. Preferably, the concentration of the extender probe is substantially lower than that of the polydeoxynucleotide primer. By "substantially lower" is meant that the concentration of extender probe relative to primer is at least 1 to 10, usually 1 to 100 or more. Preferably, the concentration of the extender probe is less than one percent that of the polydeoxynucleotide primer.

Figure 6:
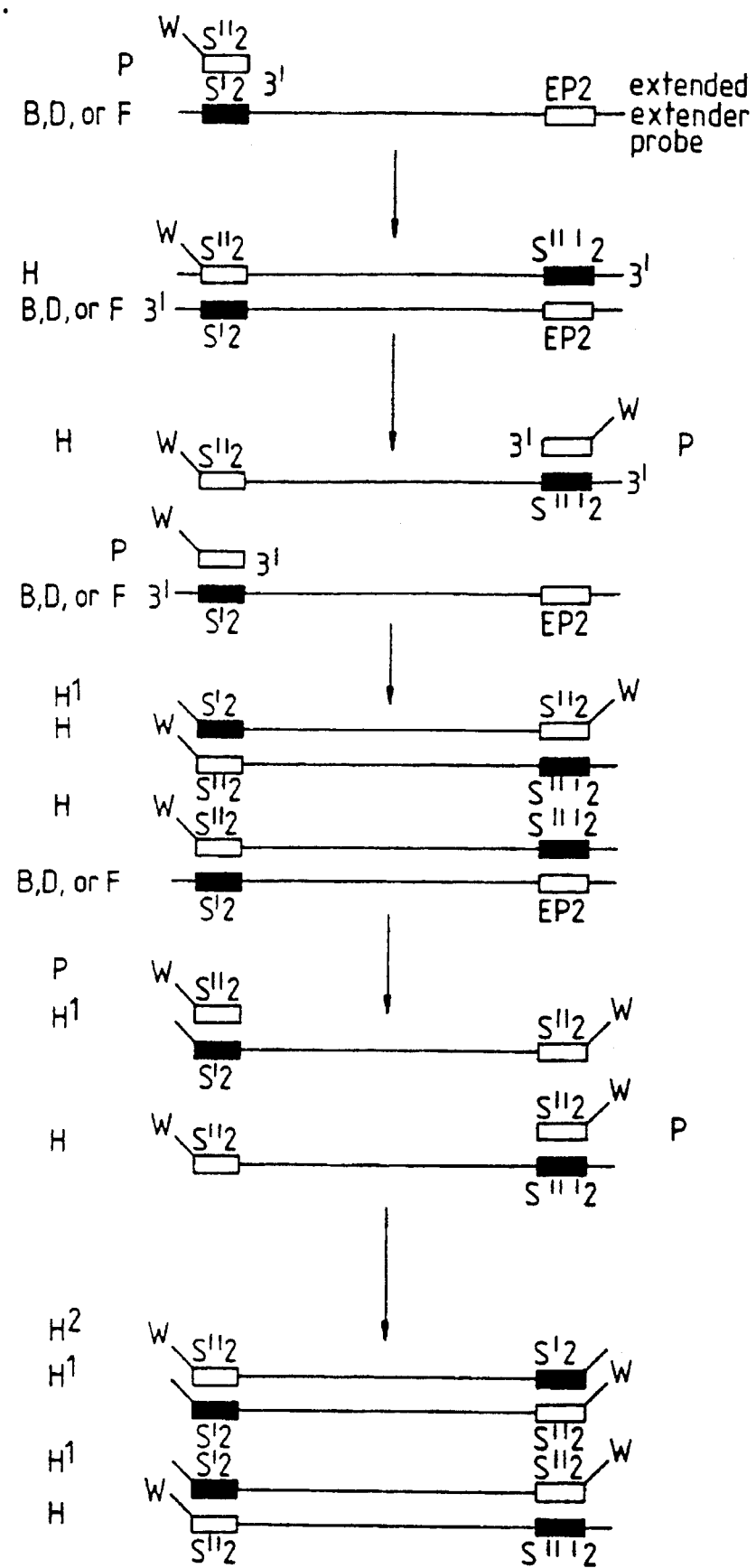
FIG. 6 is a schematic of another embodiment in accordance with the present invention.

The use of the present method in single primer amplification is depicted in FIG. 6.

Polydeoxynucleotide primer P has a sequence at its 3'-end (S"2) that hybridizes with S'2, wherein S'2 is complementary to S2 of the target polynucleotide sequence. Preferably, S"2 is a sequence identical to S2. P can also comprise a label W. P is hybridized with and extended along extended extender probe B (FIG. 1), D (FIG. 2) or F (FIG. 3), (which has been dissociated from its duplex) to form extended primer H comprising sequences S"2 and S'"2, S'"2 is complementary to EP2 and preferably identical to S'2. B, D or F and H are dissociated and P hybridizes with S'"2 of H and S'2 of B, D or F and P is extended along B, D or F and H to yield H and $H^1$, respectively. $H^1$ has complementary sequences S'2 and S"2. The duplexes are dissociated and P is hybridized with and extended along $H^1$ and H to yield $H^1$ and $H^2$. Further repetition results in multiple copies of $H^1$ and $H^2$, which can be detected because of the presence of label W.

Figure 7:
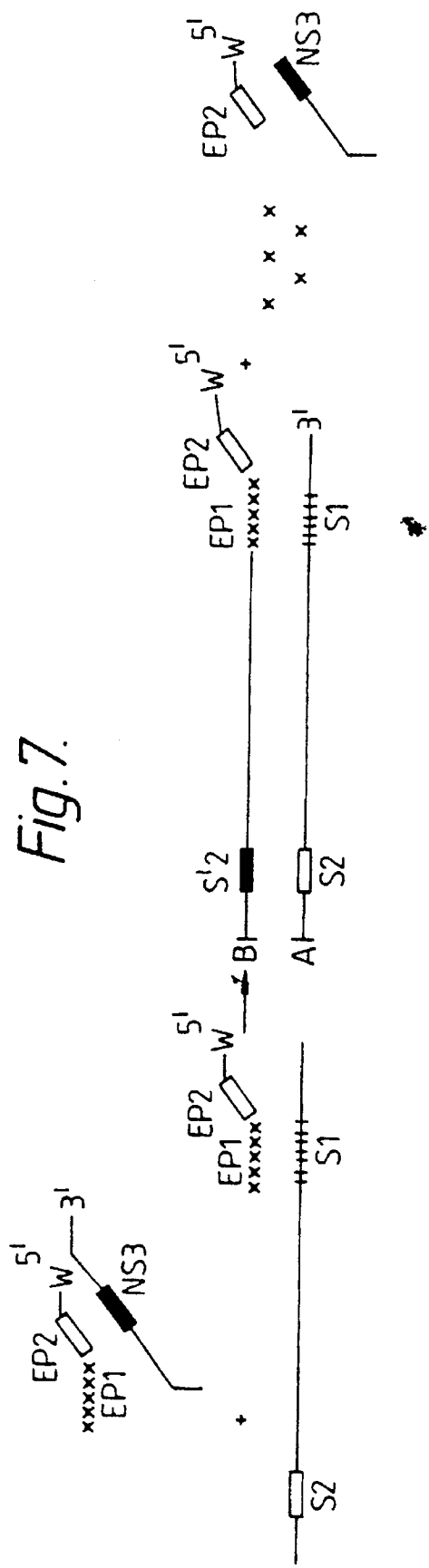
FIG. 7 is a schematic of another embodiment in accordance with the present invention.

In one embodiment of the invention the present method can be utilized to modify the 3'-end of the extender probe and form the polydeoxynucleotide primer in situ. This embodiment is depicted in FIG. 7. The extender probe contains EP1 and EP2, wherein EP2 is equivalent to primer sequence S"2 and optionally may contain a label W. EP1 of the extender probe hybridizes with S1 of the target polynucleotide sequence and with a sequence within a scavenger polynucleotide, NS3, which is complementary with at least a portion of EP2. S2 is homologous with EP2. The extender probe is extended along A to produce an extended extender probe B containing sequence S'2, which is complementary to S2. B now contains EP2 and S'2, which are hybridizable with each other. Extender probe hybridized to NS3 is degraded by an exonuclease having 3' activity, which is added to the reaction medium. The extender probe is constructed such that its degradation produces polydeoxynucleotide primer P, which is utilized in single primer amplification. Accordingly, NS3 hybridizes with EP2, at least at its 3'-end, so that EP1 is degraded by the exonuclease leaving EP2 at the 3'-end of the remaining polynucleotide. Reaction conditions are chosen such that further degradation is impeded by the presence of a double strand formed by NS3 hybridized to EP2.

Figure 8:
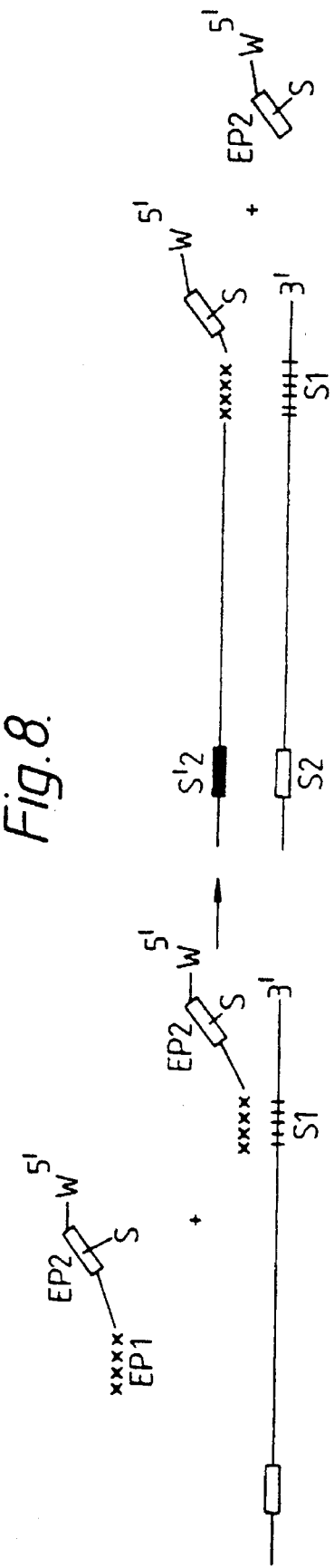
FIG. 8 is a schematic of another embodiment in accordance with the present invention.

Another convenient approach to control degradation of the extender probe so as to produce the polydeoxynucleotide primer in situ is depicted in FIG. 8. It involves the use of a 3'-exonuclease and one or more phosphorothioate diesters (indicated in FIG. 8 by S) in place of phosphate diesters between the ultimate and penultimate nucleosides at the 3'-end of EP2. Degradation of extender probe that is not bound to the target polynucleotide sequence will stop at the phosphorothioate diester or one or more nucleotides 3' of said phosphorothioate. The degraded extender probe has the sequence EP2 at its 3'-end with a phosphorothioate near the 3'-end and functions as a primer P to chain extend in accordance with single primer amplification. In this embodiment EP2 and S"2 are identical.

When the present method is applied to replicating a target polynucleotide sequence, one of the above described embodiments is followed and the following steps are repeated at least once: (a) the polydeoxynucleotide primer is caused to hybridize with and extend along the extended extender probe to form a second duplex comprising extended primer and (b) the extended primer is dissociated from the second duplex. Normally this process will be repeated at least three times whereupon the primer also is hybridized with and is extended along the extended primer to form a duplex comprising the extended primer which is thereupon dissociated. Preferably, at least a fifteen nucleotide sequence EP1 of the extender probe hybridizes with S1. Preferably, also, the polydeoxynucleotide primer contains at least a fifteen deoxynucleotide sequence S"2 capable of hybridizing with a sequence complementary to S2.

Preferably, S1 and S2 each respectively contain from 10 to 100 nucleotides. The method has application where the target polynucleotide sequence is DNA or RNA. In one aspect the polydeoxynucleotide primer is labeled with a reporter molecule. The reporter molecule can be, for example, a detectable group or a binder such as biotin or a nucleotide sequence other than the sequence that hybridizes with the sequence complementary to S2. The extended primer can be detected by means of a reporter molecule covalently bonded to a probe. The probe will usually have a nucleotide sequence that is homologous or complementary to a portion of the target nucleotide sequence other than S1 or S2.

Another embodiment of the invention concerns a method for detecting the presence of a polynucleotide analyte in a sample suspected of containing the polynucleotide analyte. A medium containing the sample is treated as described above to form a single stranded target polynucleotide sequence from the polynucleotide analyte, if present. The target polynucleotide sequence has two non-contiguous, non-complementary nucleotide sequences S1 and S2 wherein S2 is 5' of S1, and is at least ten nucleotides long. The medium is combined with an extender probe having two deoxynucleotide sequences. The sequence at the 3'-end of the extender probe (EP1) is hybridizable with S1. The other of the deoxynucleotide sequences (EP2) is homologous to S2. Means for modifying the 3'-end of extender probe not hybridized with the target nucleotide sequence is included. A polydeoxynucleotide primer capable of hybridizing with a nucleotide sequence complementary to S2 is included when modification of the extender probe does not provide a primer. Deoxynucleoside triphosphates and one or more polydeoxynucleotide polymerases are also combined. Conditions are chosen such that (1) the extender probe is hybridized with and is extended along the target polynucleotide sequence to form a duplex, (2) the extender probe not hybridized with the target polynucleotide sequence is modified, (3) the extended extender probe is dissociated from the duplex, (4) the primer hybridizes with and is extended along the extended sequence to form a second duplex comprising extended primer, (5) the extended primer is dissociated from the duplex, and (6) the primer hybridizes with and is extended along said extended primer to form a duplex comprising extended primer. Steps (5) and (6) are repeated and steps (a) and (b) are performed concomitantly or wholly or partially sequentially. Then, an examination is conducted for the presence of the extended primer, the presence thereof indicating the presence of the polynucleotide analyte. Steps (5) and (6) are repeated a least three times, preferably, at least 10 times; usually it is preferable that the number of repetitions be less than 30. Generally, steps (5) and (6) are repeated a number of times sufficient to provide an accurate detection of the polynucleotide analyte. Where the polynucleotide analyte is RNA, the polydeoxynucleotide polymerase comprises a reverse transcriptase.

In carrying out the method of forming the single stranded polydeoxynucleotide using an extender probe, modifying the extender probe not hybridized to a target polynucleotide sequence and the amplification, an aqueous medium will be employed. Other polar cosolvents may also be employed, usually oxygenated organic solvents of from 1–6, more usually from 1–4, carbon atoms, including alcohols, ethers and the like. Usually these cosolvents will be present in less than about 70 weight percent, more usually in less than about 30 weight percent.

The pH for the medium will usually be in the range of about 4.5 to 9.5, more usually in the range of about 5.5–8.5, and preferably in the range of about 6–8. The pH and temperature are chosen and varied, as the case may be, so as to cause, either simultaneously or sequentially, dissociation of any internally hybridized sequences, hybridization of the extender probe with the target polynucleotide sequence and any other sequence that forms part of the means for modifying the 3'-end of the extender probe, hybridization of the polydeoxynucleotide primer with extended extender probe and extended primer, extension of the extender probe and primer, degradation of the 3'-end of the extender probe by an exonuclease, dissociation of the extended extender probe and extended primer. In some instances, a compromise will be made in optimizing the speed, efficiency, and specificity of these steps depending on whether it is desired to perform the above steps performed sequentially or simultaneously. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

Moderate temperatures are normally employed for carrying out the method. Normally, in conducting the method the medium will be cycled between two or three temperatures. The temperatures for the method will generally range from about 10° to 105° C., more usually from about 40° to 99° C., preferably 50° to 98° C. The exact temperatures can be varied depending on the salt concentration, pH, solvents used, length of the target and S1 and S2 sequences and composition of the target polynucleotide sequence and the primer. Relatively low temperatures of from about 30° to 65° C. can be employed for the extension steps, while denaturation and hybridization can be carried out at a temperature of from about 50° to 105° C. Degradation of the 3'-end of the extender probe by an exonuclease is usually conducted at a temperature of about 15° to 100° C., preferably 20° to 50° C.

The time period for carrying out the modification of the 3'-end of the extender probe not hybridized to a target polynucleotide sequence will generally be about 0.5 to 30 minutes, preferably 1 to 20 minutes. Where the present method is utilized in single primer amplification, the method is conducted for a time sufficient to achieve a desired number of copies of the extended primer or a sequence complementary thereto. This, in turn, depends on the purpose for which the amplification is conducted, such as, for example, an assay for a polynucleotide analyte. Generally, the time period for conducting the method will be from about 1 to 10 minutes per cycle and any number of cycles can be used from 1 to as high as 200 or more, usually 5 to 80, frequently 10–60. As a matter of convenience it will usually be desirable to minimize the time period and the number of cycles. In general, the time period for a given degree of amplification can be shortened, for example, by selecting concentrations of nucleoside triphosphates sufficient to saturate the polynucleotide polymerase and by increasing the concentrations of polynucleotide polymerase and polynucleotide primer. Generally, the time period for conducting the method will be from about 5 to 200 minutes. As a matter of convenience, it will usually be desirable to minimize the time period.

The above conditions may also be chosen for forming a target polynucleotide sequence from a polynucleotide analyte.

The amount of reagents for modifying the 3'-end of the extender probe varies depending on the particular means for achieving the modification. In the situation wherein modification involves extension of the 3'-end of the extender probe, the concentration of the template dependent polynucleotide polymerase and the deoxynucleotide triphosphates will generally be equal or more than that described below for the amplification and may require a different enzyme. The concentration of reagents utilized for the extension of the extender probe along the target polynucleotide sequence and amplification will be sufficient to extend the extender probe not bound to the target polynucleotide sequence. The concentration of any scavenger polynucleotide sequence will generally be at least as great as the concentration of extender probe and usually at least 10-fold higher.

Where modification of the extender probe is accomplished by means of a 3' exonuclease, the concentration of the exonuclease is selected to degrade the extender probe to the desired extent in a practical time period such as 0.5–20 minutes. Preferably, the template dependent polynucleotide polymerase will also have 3' exonuclease activity, and, thus, the concentration of this polymerase will be chosen to be sufficient to accomplish chain extension and degradation. Usually, when the 3'-end of the extender probe is to be completely degraded, the magnesium ion concentration in the initial enzyme reaction is kept low (less than 4 mM, for example) and the pH remains high (greater than 8.0, for example).

The concentration of the extender probe, as mentioned above, can be substantially less than that of the primer. Preferably, the extender probe concentration is less than one percent of that of the primer, more preferably less than 0.1% that of the primer usually the extender probe concentration will be less than 1 nmolar, frequently less than 0.1 nmolar (nM) whereas the primer concentration will usually be greater than 10 nmolar, usually at least 100 nmolar. Preferably, the concentration of primer is greater than 100 nM while that of the extender probe is less than 1 nM.

The amount of the target polynucleotide sequence which is to be copied can be as low as one or two molecules in a sample but will generally vary from about $10^2$ to $10^{10}$, more usually from about $10^3$ to $10^8$ molecules in a sample preferably at least $10^{-21}$M in the sample and may be $10^{-10}$ to $10^{-19}$M, more usually $10^{-14}$ to $10^{-19}$M. The amount of the polydeoxynucleotide primer will be at least as great as the number of copies desired and will usually be $10^{-13}$ to $10^{-8}$ moles per sample, where the sample is 1–1,000 μL. Usually, the primer will be present in at least $10^{-9}$M, preferably $10^{-7}$M, and more preferably at least about $10^{-6}$M. Preferably, the concentration of the polynucleotide primer is substantially in excess over, preferably at least 100 times greater than, the concentration of the single stranded polynucleotide.

The concentration of the deoxynucleoside triphosphates in the medium can vary widely; preferably, these reagents are present in an excess amount. The deoxynucleoside triphosphates will usually be present in $10^{-6}$ to $10^{-2}$M, preferably $10^{-5}$ to $10^{-3}$M.

The concentration of the template-dependent polynucleotide polymerase will usually be determined empirically. Preferably, a concentration will be used that is sufficient such that further increase in the concentration will not decrease the time for the amplification by over 5-fold, preferably 2-fold. The primary limiting factor generally is the cost of the reagent.

The order of combining of the various reagents to form the combination may vary. Generally, the target polynucleotide sequence is obtained from a sample containing such sequence or a polynucleotide analyte that has been treated to obtain such sequence. Generally, the target polynucleotide sequence and the extender probe are combined with a pre-prepared combination of any polynucleotide sequence needed for modification of the 3'-end of the extender probe not bound to the target polynucleotide sequence, deoxynucleoside triphosphates, template-dependent polydeoxynucleotide polymerase and a 3' exonuclease where appropriate. Where needed, a polynucleotide primer may be included in the prepared combination or may be added subsequently. However, simultaneous addition of all of the above, as well as other step-wise or sequential orders of addition, may be employed.

The concentration and order of addition of reagents and conditions for the method are governed generally by the desire to maximize the number of copies of the extended primer and the rate at which such copies are formed and the fidelity of replication. Generally, it is desirable to increase the number of copies of the extended primer by at least a factor of $10^2$, preferably a factor of $10^4$, more preferably $10^6$ or more.

In carrying out the method of the invention as applied to the detection of a polynucleotide analyte, the considerations as to media, pH, temperature, and times can be as described above.

While the concentrations of the various reagents will generally be determined by the concentration range of interest of the polynucleotide analyte, the final concentration of each of the reagents will normally be determined empirically to optimize the sensitivity of the assay over the range of interest. The concentration of the other reagents in an assay generally will be determined following the same principles as set forth above for the amplification method. The primary consideration is that a sufficient number of copies of extended primer be produced, free of any extender probe, in relation to the polynucleotide analyte sequence so that such copies can be readily detected and provide an accurate determination of the polynucleotide analyte.

The copies of extended primer can be detected in numerous ways. For example, in the present method, molecules of the polydeoxynucleotide primer can be labeled with a reporter molecule such as a ligand, a small organic molecule, a polynucleotide sequence, a protein, support, a member of an operator-repressor pair, intercalation dye and the like.

Examples of particular labels or reporter molecules and their detection can be found in U.S. patent application Ser. No. 07/555,968 filed Jul. 19, 1990, now U.S. Pat. No. 5,439,998 the relevant disclosure of which is incorporated herein by reference.

Other assay formats and detection formats are disclosed in U.S. patent applications Ser. Nos. 07/229,282 filed Jan. 19, 1989, now U.S. Pat. No. 5,508,178 and 07/399,795 filed Aug. 29, 1989, respectively, which have been incorporated herein by reference.

Any standard method for specifically detecting nucleic acid sequences can be used.

One method for detecting nucleic acids is to employ nucleic acid probes.

One method utilizing probes is described in U.S. patent application Ser. No. 773,386, filed Sep. 6, 1985 now U.S. Pat. No. 4,868,104 the disclosure of which is incorporated herein by reference.

Detection of the signal will depend upon the nature of the signal producing system utilized. If the label or reporter group is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule the medium can be irradiated and the fluorescence determined. Where the label is a radioactive group, the medium can be counted to determine the radioactive count.

Various techniques can be employed for preparing an extender probe, polydeoxynucleotide primer, or other polynucleotide sequences utilized in the present invention. They can be obtained by biological synthesis or by chemical synthesis. For short sequences (up to about 100 nucleotides) chemical synthesis will frequently be more economical as compared to the biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide binding sequence. The extender probe, polydeoxynucleotide primer and other polynucleotides can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described by J. Messing (1983) *Methods Enzymol,* 101, 20–78.

Other methods of oligonucleotide synthesis include phosphotriester and phosphodiester methods (Narang, et al. (1979) *Meth. Enzymol* 68:90) and synthesis on a support (Beaucage, et al. (1981) *Tetrahedron Letters* 22: 1859–1862) as well as phosphoramidate technique, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

Extender probes containing at least one phosphorothioate diester can be prepared according to known techniques. Oligonucleotide synthesis can be carried out as described above up to the point where introduction of the phosphorothioate diester is desired. The phosphorothioate diester can be introduced in a number of ways such as, for example, oxidations utilizing a thiolating reagent such as a diacyldisulfide or tetraethyl thiuram disulfide, which are commercially available. The remaining nucleotides are then introduced. Other methods of preparing phosphorothioate containing polynucleotides are described in WO9008838, WO8911486, U.S. Pat. No. 4,910,300, EP318245, the relevant disclosures of which are incorporated herein by reference. Other methods of preparing a phosphorothioate containing polynucleotide are described by (a) Yau, et al., *Tetrahedron Lett.* (1990)31(14): 1953–1956; (b) Brill, et al., ibid. (1989) 30(48):6621–6624; (c) Caruthers, et al., *Nucleic Acids Symp. Ser.* (1989)21: 119–120; (d) Caruthers, et al., *Nucleosides Nucleotides* (1988)8(5–6): 1011–1014; (e) Brill, et al., *J. Am. Chem. Soc.* (1989)111(6): 2321–2322.

In some instances, the 3'-end of a polynucleotide will be modified to prevent reaction with template dependent DNA polymerase or to append a binding sequence. The 3'-end can, for example, be modified by ligation of a dideoxynucleotide or a ribonucleotide followed by oxidation of the ribose with periodate followed by reductive amination of the resulting dialdehyde with borohydride and a bulky amine such as aminodextran.

As a matter of convenience, predetermined amounts of reagents employed in the present invention can be provided in a kit in packaged combination. In assaying for a polynucleotide analyte in a sample, a kit useful in the present method can comprise, in packaged combination with other reagents, reagents for forming a target polynucleotide sequence from a polynucleotide analyte, an extender probe having at its 3'-end a sequence hybridizable with a first sequence in a target polynucleotide sequence and having a sequence that is homologous to a second sequence of the target polynucleotide sequence, wherein the second sequence is 5' and non-contiguous with the first sequence, and a polydeoxynucleotide primer, the latter of which can be labeled or can be provided with groups to render the sequence labeled or bound to a support. The kit can further include a labeled polynucleotide probe capable of binding to the target polynucleotide sequence, any polynucleotide sequences necessary for modifying the 3'-end of extender probe not hybridized to the target polynucleotide sequence and also, where appropriate, a 3' exonuclease. The kits above can further include in the packaged combination deoxynucleoside triphosphates such as deoxynucleoside triphosphates, e.g., deoxyadenosine triphosphate (dATP), deoxyguanosine triphosphate (dGTP), deoxycytidine triphosphate (dCTP) and deoxythymidine triphosphate (dTTP). For use in a method of producing multiple copies, the kit can contain a polydeoxynucleotide primer if the primer is not produced by degradation of the extender probe. The kit can further include a polydeoxynucleotide polymerase and members of a signal producing system and also various buffered media, some of which may contain one or more of the above reagents.

The relative amounts of the various reagents in the kits can be varied widely to provide for concentrations of the reagents which substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life will permit.

EXAMPLES

The invention is demonstrated further by the following illustrative examples. Temperatures are in degrees centigrade (° C.) and parts and percentages are by weight, unless otherwise indicated.

Example 1

Modification of Extender Probe by Exonuclease Degradation
Oligodeoxyribonucleotide sequences 1 and 2:

Polynucleotide extender probe;
Oligomer 1
5' TGT TGT TCC GTT AGT TCG TTT TAT TTG TCG AAA TCC GCG ACC TGC TCC ATG TTA CT3' (SEQ. No. 1), and
Polydeoxynucleotide primer for amplification;
Oligomer 2
5' TGT TGT TCC GTT AGT TCG TTT TAT T 3' (SEQ. No. 2)

were synthesized by the phosphoramidite method (Atkinson, T. and Smith, M. in *Oligonucleotide Synthesis: A Practical Approach*, Gait, M. J. (ed.), IRL Press, Oxford, England (1984)) and purified on denaturing polyacrylamide gels according to standard procedures. The 25-5' terminal bases of extender probe oligomer 1 were identical to polydeoxynucleotide primer oligomer 2 and were used to generate an amplifiable polynucleotide sequence having an intramolecular base pair structure.

A protocol for DNA amplication of target polynucleotide bacteriophage M13mp19 (double-stranded replicative form, 7250 base pairs from Bethesda Research Laboratories) using oligomer 1 to form the initial amplifiable structure and subsequently oligomer 2 to drive the amplification was utilized. Ten picomoles (pmol) of oligomer 1 and 600 molecules of M13mp19 were combined in a buffer of 10 mM KCl, 10 mM $(NH_4)_2SO_4$, 20 mM Tris-CHl (pH 8.8 @25° C.), 2 mM $MgSO_4$, 0.1% Triton X-100, and 20 nanomoles (nmoles) of each dNTP. After the reaction mixture was denatured at 95° C. for 5 minutes and cooled to room temperature to allow annealing of the extender probe oligomer 1 to the template, 5 units of T7 DNA polymerase (New England Biolabs), 5 units of T4 DNA polymerase (Bethesda Research Laboratories) or 4 units of Klenow fragment (U.S. Biochemical) was added to the reaction and incubated at 37° C. for 5–10 minutes. During this incubation, any extender probe oligomer 1, which was not annealed to the target polynucleotide was degraded by the 3' to 5' exonuclease activity of the above enzymes. Any extender probe which annealed to the target polynucleotide was extended by the polymerase activity of the enzymes to form the amplifiable polynucleotide having an intramolecular base paired structure. The T7, T4, or Klenow polymerase was then heat inactivated by incubation at 95° C. for 2 minutes and the mixture Was again cooled to room temperature. 100 pmoles of oligomer 2 and 1 to 2 units of Vent DNA polymerase (New England Biolabs) were then added for a final volume of 100 microliters (μl). Temperature cycling of 90° C. (30 seconds), 55° C. (1 minute), and 72° C. (5 minutes for the first 10 cycles and 1.5 minutes thereafter) was performed using a programmable thermal cycler (Ericomp, Inc.) for a number of cycles through the above three temperatures. Aliquots from these reactions were withdrawn at the conclusion of temperature cycling and were analyzed by electrophoresis through 1.2% agarose (Seakem GTG, FMC BioProducts) gels in 1X TAE buffer [40 mM Tris-Acetate (pH 10.3 @23° C.), 10 mM EDTA] and the DNA products were visualized by staining the gel with ethidium bromide.

In order to confirm that the treatment with the 3' to 5' exonuclease completely removed any extender probe oligomer 1 not annealed to the target polynucleotide from the reaction, a trace amount of extender oligomer 1 labeled at the 5'-end with 32P using T4 polynucleotide kinase (USB) was included in the reaction. An aliquot was removed after the exonuclease incubation and analyzed by denaturing polyacrylamide gel electrophoresis followed by autoradiography. Results obtained from this experiment are summarized in Table 1.

TABLE 1

| 3' to 5' exonuclease treatment | Target DNA | Extender probe present after cycle 1 | Amplification after 60 cycles |
|---|---|---|---|
| − | none | + | − |
| + | none | − | − |
| − | 600 molecules | + | + |
| + | 600 molecules | − | + |

The results in Table 1 demonstrate that treatment of the reaction mixture with a DNA polymerase which possesses a 3' to 5' exonuclease activity, after annealing of the extender probe 1 oligomer to the target polynucleotide but before the addition of the amplification polydeoxynucleotide primer and the thermostable DNA polymerase, completely removed all of the extender probe oligomer 1 from the reaction and permitted the formation of enough polynucleotide having an intramolecular base paired structure to allow amplification from 600 double-stranded DNA targets.

Example 2

Modification of Extender probe by Chain Extension
Oligodeoxyribonucleotide sequences 1 and 2:

Polynucleotide extender probe;
Oligomer 1
5' TAG CTA GCA GTA ACA TGG AGC AGT GTT GTT CCG TTA GTT CGT TTT ATT TGT CGA AAT CCG CGA CCT GCT CCA TGT TAC T 3' (SEQ. No. 3), and
Polydeoxynucleotide primer;
Oligomer 2
5' TGT TGT TCC GTT AGT TCG TTT TAT T 3' (SEQ. No. 4)

were synthesized by the phosphoramidite method and purified on denaturing polyacrylamide gels. Contained within oligomer 1 is the entire sequence of oligomer 2 (bases 24–48), which were used to generate an amplifiable polynucleotide having an intramolecular base paired structure. Bases 9–23 and 65–79 of oligomer 1 comprise an inverted repeat, which is capable of forming an intramolecular base paired structure consisting of a 15 basepair stem and a 41 base loop. The eight 5' terminal bases of oligomer 1 are not complementary to the target polynucleotide, i.e., bacteriophage M13mp19.

A protocol for DNA amplification of bacteriophage M13mp19 (double-stranded replicative form, 7250 base pairs) using extender probe oligomer 1 to form the initial polynucleotide having an intramolecular base paired structure and subsequently oligomer 2 to drive the amplification was utilized. Ten picomoles (pmol) of oligomer 1, 200 pmoles of oligomer 2, and 600 molecules of M13mp19 were combined in a buffer of 10 mM KCl, 10 mM $(NH_4)_2SO_4$, 20 mM Tris-HCl (pH 8.8 @25° C.), 2 mM $MgSO_4$, 0.1% Triton X-100, and 20 nanomoles (nmoles) of each dNTP. The reaction mixture was denatured at 95° C. for 5 minutes and cooled to room temperature to allow annealing of extender probe oligomer 1 to the target DNA. One to two units of Vent DNA polymerase (New England Biolabs) was then added for a final volume of 100 microliters (μl). The reactions were then incubated at 72° C. for 10 minutes. During this step any extender probe oligomer 1 that annealed to the target polynucleotide was extended by Vent polymerase to form an intramolecular base paired (bp) structure, which was amplified by oligmer 2. Any extender probe oligomer 1 not annealed to the target polynucleotide formed an intramolecular stem-loop containing a 15 bp stem and an 8 base 5' single-stranded overhang. This 5' overhang was filled in by Vent polymerase with the complementary nucleotides. Since the 8 bases filled in by Vent polymerase were not complementary to the target polynucleotide, the modified extender probe oligomer 1 was rendered inactive as a primer. Any of this extender probe that may still anneal to the target has an 8 base mismatch at the 3'-end and thus can not be extended by Vent polymerase.

Temperature cycling of 90° C. (30 seconds), 55° C. (1 minute), and 72° C. (5 minutes for the first 10 cycles and 1.5 minutes thereafter) was performed using a programmable thermal cycler (Ericomp, Inc.) for a number of cycles through the above three temperatures. Aliquots from these reactions were withdrawn at the conclusion of temperature cycling and were analyzed by electrophoresis through 1.2% agarose (Seakem GTG, FMC BioProducts) gels in 1XTAE buffer [40 mM Tris-Acetate (pH 10.3 @23° C.), 10 mM EDTA] and the DNA products were visualized by staining the gel with ethidium bromide.

In order to confirm that all unannealed extender oligomer probe 1 was filled in by the action of Vent polymerase using deoxynucleotide triphosphates during the initial incubation at 72° C. a trace amount of extender probe oligomer 1 that had been labeled at the 5'-end with $^{32}P$ using T4 polynucleotide kinase (USB) was included in the reaction. An aliquot was removed after the initial incubation at 72° C. and analyzed by denaturing polyacrylamide gel electrophoresis followed by autoradiography. Results obtained from this experiment are summarized in Table 2:

TABLE 2

| Target DNA | Fill-in of extender probe after cycle 1 | Amplification after 60 cycles |
| --- | --- | --- |
| None | + | − |
| 600 molecules | + | + |

The results in Table 2 demonstrate that, in the presence of 600 double-stranded DNA targets, the extender probe oligomer formed an internal base paired structure or stem loop with a 5' single stranded overhang, which was effectively filled-in by Vent polymerase by the end of the first cycle of amplification, thereby preventing it from serving as a primer in subsequent rounds of amplification. The amplification primer then efficiently drove the amplification of the amplifiable intramolecular base paired structures that were formed in the initial cycle.

Example 3

Modification of Extender Probe Utilizing a Phosphorothioate- containing Oligonucleotide The detection of approximately 600 double-stranded target molecules using single primer amplification was demonstrated repeatedly using a degradable, phosphorothioate-containing oligonucleotide. The oligonucleotide (56 bases) acts as the extender probe in creating an amplifiable stem-loop and, following nuclease treatment, serves as a primer to drive amplification.

The synthesis of the extender probe oligonucleotide was carried out in an automated (4-column Biosearch 8750 DNA synthesizer) manner until positioning of the thio-modified linkage(s). Manual oxidations were then performed with 0.1M tetraethyl thiuram disulfide (TETD) (Applied Biosystems, Inc., Foster City, Calif.) in acetonitrile. The remaining bases were added under normal coupling conditions following the protocol in Applied Biosystems, Inc., User Bulletin, Number 58, February 1991. In present example, two different extender probes, identical in sequence, differing only in the number and position of the phosphorothioate internucleotidic linkage(s) as seen below, were employed, one each in separate experiments.

The formation and amplification of a stem-loop molecule was carried out in 100 microliter reactions containing an appropriate buffer (20 mM Tris-HCl, pH 8.8, 10 mM KCl, 10 mM $(NH_4)_2SO_4$, 2 mM $MgSO_4$, and 0.1% Triton X-100), dNTPs (200 to 300 micromolar), double stranded target polynucleotide molecule (600 M13mp19 molecules,), and the extender probe (0.5 to 4 micromolar initial concentration). Reactants were heat-denatured for 5 minutes at 95° C. and annealed at 25° C. (room temperature) for 15 to 20 minutes. A DNA polymerase with a strong 3' exonuclease activity was added (10 units per 100 μl of T7 DNA polymerase, New England Biolabs (NEB), Beverly Mass.). Reactions were incubated at 37° C. such that any extender probe annealed to target was chain extended, whereas all non-annealed extender probe was degraded up to the position(s) of the thio linkage(s). The extender probe was radiolabelled at the 5'-end to monitor degradation. Complete degradation of the non-annealed extender probe up to the thio linkage(s) was obtained in as little as 1 minute, while the remaining sequence was resistant to further degradation for up to 15 minutes. After the elongation/degradation was complete, reactants were again heated at 95° C. for 1 to 2 minutes, thereby inactivating the T7 polymerase and denaturing the newly formed stem-loop molecule from the original target molecule. A heat-stable polymerase was added (Pfu from Stratagene San Diego, Calif., 5 units per 100 μl) and the reactions are cycled in a format as described in the previous examples. Aliquots from these reactions are analyzed by electrophoresis through 1.2% agarose (Seakem, FMC Bio Products) gels in 1× TBE buffers [89 mM Tris-borate, 89 mM boric acid, 0.2 mM EDTA] and the amplified product was visualized by ethidium bromide staining.

Extender Probes containing thio linkage(s):
  1. One phosphorothioate linkage between $A_{34}$ and $T_{35}$:
     a) 23 base primer remained after degradation (underlined)

3' TC ATT GTA CCT CGT CCA GCG CCT AAA GCT G T T T A T T

T T G C T T G A T TGCCTTGTTGT 5' (SEQ. No. 5)

2. Three phosphorothioate linkages between $T_{33}$ and $T_{36}$:
a) mixture of 3 primers (24, 23, 22 bases) remained after degradation (underlined)

3' TC ATT GTA CCT CGT CCA GCG CCT AAA GCT G T T T A T T

T T G C T T G A T TGCCTTGTTGT 5' (SEQ. NO. 6)

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in the art such as molecular biology and related sciences are intended to be within the scope of the following claims.

What is claimed is:

1. A method for forming, from an extender probe, which maybe extended or modified, and a single stranded target polynucleotide sequence, a polynucleotide, said polynucleotide being complementary to an extended extender probe and having a sequence identical to said target polynucleotide sequence attached at its 3'-end to a polynucleotide sequence complementary to a polynucleotide sequence at the 5' end of said target polynucleotide sequence, wherein during said method said extender probe is modified to enhance the efficiency of said forming of said polynucleotide by reducing the priming effectiveness of said extender probe, said method comprising:

(a) hybridizing to a sequence S1 at the 3'-end of said single stranded target polynucleotide sequence the 3'-end of said extender probe wherein said extender probe contains a sequence substantially identical to a sequence S2 at the 5'-end of said single stranded target polynucleotide sequence and wherein said S1 and said S2 are non-complementary and separated from one another by at least 10 nucleotides, (b) extending, by means of a polydeoxynucleotide polymerase and deoxynucleoside triphosphates, said extender probe along said single stranded target polynucleotide sequence to produce an extended extender probe, (c) extending or degrading by means of an enzyme said 3'-end of said extender probe not hybridized to said single stranded target polynucleotide sequence to produce a modified extender probe, (d) hybridizing a primer to the 3'-end of the extended extender probe, said primer having said sequence S2 at its 3'-end, and (e) extending, by means of a polydeoxynucleotide polymerase and deoxynucleoside triphosphates, said primer along said extended extender probe, thereby forming said polynucleotide having a sequence identical to said target polynucleotide sequence attached at its 3'-end to a polynucleotide sequence complementary to a polynucleotide sequence at the 5' end of said target polynucleotide sequence.

2. A method for producing from an extender probe a polydeoxynucleotide, said polydeoxynucleotide being an extended extender probe and having two segments that are non-contiguous and complementary with each other, wherein during said method said extender probe is modified to reduce the priming effectiveness thereof in an amplification of said polydeoxynucleotide, said method comprising:

providing in combination (a) a polynucleotide having two non-contiguous, non-complementary nucleotide sequences S1 and S2 wherein S2 is 5' of S1 and is at least ten nucleotides long wherein said S1 and S2 are separated by at least 10 nucleotides, (b) an extender probe comprised of two deoxynucleotide sequences, wherein the sequence at the 3'-end of said extender probe, EP1, hybridizes with S1 and the other of said deoxynucleotide sequences, EP2, is homologous to S2, and (c) an enzyme for chemically modifying the 3'-end of said extender probe that does not hybridize with said polynucleotide, and extending, by means of a polydeoxynucleotide polymerase and polydeoxynucleoside triphosphates, said extender probe along said polynucleotide to produce extended extender probe which is said polydeoxynucleotide having two segments that are non-contiguous and complementary with each other, wherein the 3'-end of said extender probe not hybridized with said polynucleotide is extended or degraded by means of said enzyme, thereby producing modified extender probe.

3. The method of claim 2 wherein said enzyme is for extending the 3'-end of said extender probe.

4. The method of claim 3 wherein said combination further comprises a nucleotide sequence EP3 that hybridizes with said EP2.

5. The method of claim 3 wherein said combination further comprises a nucleotide sequence EP3 in said extender probe, wherein said extender probe not hybridized with the target polynucleotide sequence forms a loop and said EP3 hybridizes with said EP2.

6. The method of claim 3 wherein said EP3 is 3' of said EP2.

7. The method of claim 3 wherein said EP3 is 5' of said EP2.

8. The method of claim 2 wherein said enzyme is for degrading the 3'-end of said extender probe.

9. The method of claim 8 wherein said enzyme is an enzyme having 3'-exonuclease activity.

10. The method of claim 2 which further comprises replicating said polydeoxynucleotide by providing in said combination a polydeoxynucleotide primer that hybridizes at least at its 3'-end with a nucleotide sequence complementary to S2 under conditions where (1) said extended extender probe is rendered single stranded, (2) said polydeoxynucleotide primer hybridizes with and is extended along said extended extender probe to form a duplex comprising extended primer, (3) said extended primer is dissociated from said duplex, and (4) said polydeoxynucleotide primer hybridizes with and is extended along said extended primer to form a duplex comprising extended primer.

11. The method of claim 10 wherein said polydeoxynucleotide primer is comprised of sequence EP2 at its 3'-end and conditions are provided where (1) said extended extender probe is rendered single stranded, (2) said polydeoxynucleotide primer hybridizes with and is extended along said extended extender probe to form a duplex comprising extended primer, (3) said extended primer is dissociated from said duplex, and (4) said polydeoxynucleotide primer hybridizes with and is extended along said extended primer to form a duplex comprising extended primer.

12. The method of claim 10 wherein steps (3) and (4) are repeated.

13. The method of claim 12 wherein the concentration of said extender probe is substantially lower than that of said polydeoxynucleotide primer.

14. The method of claim 12 wherein the concentration of said extender probe is less than one percent that of said polydeoxynucleotide primer.

15. A method for replicating a target polynucleotide sequence, said target polynucleotide sequence having two non-contiguous, non-complementary nucleotide sequences S1 and S2 each at least 10 nucleotides long separated from one another by at least 10 nucleotides, wherein S2 is 5' of S1 and wherein during said method said extender probe is extended or degraded to reduce the priming effectiveness thereof in further replication of said target polynucleotide sequence, said method comprising:

providing in combination, either concomitantly or wholly or partially sequentially, (1) said target polynucleotide sequence, (2) an extender probe, which may be extended or modified, having two deoxynucleotide sequences wherein the sequence at the 3'-end of said extender probe, EP1, hybridizes with S1 and the other of said deoxynucleotide sequences, EP2, is homologous to S2, (3) an enzyme for extending or degrading the 3'-end of said extender probe not hybridized with said target polynucleotide sequence, (4) a polydeoxynucleotide primer comprised of sequence S2 at its 3'-end where said polydeoxynucleotide primer may be provided directly or generated in situ, (5) DNA polymerase and (6) deoxynucleoside triphosphates under conditions wherein (A) some of said extender probe becomes hybridized with and extended along said target polynucleotide sequence to form a duplex comprising extended extender probe, (B) extender probe not hybridized to said target nucleotide sequence is extended or degraded at its 3'-end by said enzyme, (C) said extended extender probe is dissociated from said duplex, (D) said polydeoxynucleotide primer hybridizes with and is extended along said extended extender probe to form a duplex comprising extended polydeoxynucleotide primer, (E) said extended polydeoxynucleotide primer is dissociated from said duplex, and (F) said polydeoxynucleotide primer hybridizes with and is extended along said extended polydeoxynucleotide primer to form a duplex comprising extended polydeoxynucleotide primer and steps (E) and (F) are repeated, wherein said extended polydeoxynucleotide primer is a replication of said target polynucleotide sequence.

16. The method of claim 15 wherein said enzyme is for extending the 3'-end of said extender probe.

17. The method of claim 16 wherein said combination further comprises a nucleotide sequence EP3 that hybridizes with said EP2.

18. The method of claim 16 wherein said combination further comprises a nucleotide sequence EP3 in said extender probe, wherein said extender probe not hybridized with said target polynucleotide sequence forms a loop and said EP3 hybridizes with said EP2.

19. The method of claim 16 wherein said EP3 is 3' of said EP2.

20. The method of claim 16 wherein said EP3 is 5' of said EP2.

21. The method of claim 15 wherein said enzyme is for degrading the 3'-end of said extender probe.

22. The method of claim 21 wherein said enzyme is an enzyme having 3'-exonuclease activity.

23. The method of claim 21 wherein said combination further comprises a polynucleotide sequence NS3 that hybridizes with at least the 3'-end of said EP2.

24. The method of claim 23 wherein said polydeoxynucleotide primer is provided by degradation of said extender probe at least the 3'-end of which is not hybridized with the polynucleotide sequence NS3.

25. The method of claim 23 wherein said NS3 is part of said extender probe.

26. The method of claim 15 wherein steps (E) and (F) are repeated at least three times.

27. The method of claim 15 wherein the concentration of said extender probe is less than one percent that of said polydeoxynucleotide primer.

28. The method of claim 15 wherein at least a fifteen nucleotide sequence of said extender probe hybridizes with S1.

29. The method of claim 15 wherein said polydeoxynucleotide primer contains at least a fifteen nucleotide sequence identical to S2.

30. The method of claim 15 wherein S1 and S2 each respectively contain from 10 to 100 nucleotides.

31. The method of claim 15 wherein said target polynucleotide sequence is DNA.

32. The method of claim 15 wherein said polydeoxynucleotide primer contains a nucleotide sequence in addition to S2.

33. A kit comprising in packaged combination:

an extender probe having at its 3'-end a sequence (EP1) that hybridizes with a first sequence in a target polynucleotide sequence and having a sequence (EP2) that is substantially identical to a second sequence of said target polynucleotide sequence, wherein in said target polynucleotide sequence said second sequence is 5' and non-contiguous with said first sequence, a nucleotide sequence (NS) having a portion that hybridizes with EP1 wherein said NS may be a separate molecule or part of said extender probe, and a polydeoxynucleotide primer that hybridizes with a sequence that is complementary with said second sequence.

34. The kit of claim 33 wherein said NS is part of said extender probe.

35. The kit of claim 33 wherein said NS is a molecule separate from said extender probe.

36. The kit of claim 33 which comprises template dependent DNA polymerase.

37. The kit of claim 36 which comprises deoxynucleoside triphosphates.

38. The kit of claim 33 wherein said polydeoxynucleotide primer is labeled with a reporter molecule.

39. A kit comprising in packaged combination:

an extender probe having at its 3'-end a sequence that hybridizes with a first sequence (EP1) in a target polynucleotide sequence and having a sequence that is substantially identical to a second sequence (EP2) of said target polynucleotide sequence, wherein in said target polynucleotide sequence said second sequence is 5' and non-contiguous with said first sequence, an enzyme that degrades said sequence that hybridizes with said EP1 when said sequence is not hybridized to said EP1, and a polydeoxynucleotide primer that hybridizes with a sequence that is complementary with said second sequence.

40. The kit of claim 39 wherein said enzyme has 3' exonuclease activity.

41. The kit of claim 39 which comprises a nucleotide sequence (NS) that hybridizes with at least a portion of said EP2 such that, upon degradation of excess of said extender probe, said polydeoxynucleotide primer is formed in situ.

42. The kit of claim 41 wherein said NS is part of said extender probe.

43. The kit of claim 41 wherein said NS is a molecule separate from said extender probe.

44. The kit of claim 41 which comprises template dependent DNA polymerase.

45. The kit of claim 44 which comprises deoxynucleoside triphosphates.

46. The kit of claim 39 wherein said polydeoxynucleotide primer is labeled with a reporter molecule.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 56 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

TGTTGTTCCG TTAGTTCGTT TTATTGTCG AAATCCGCGA CCTGCTCCAT GTTACT    56

( 2 ) INFORMATION FOR SEQ ID NO:2:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

TGTTGTTCCG TTAGTTCGTT TTATT    25

( 2 ) INFORMATION FOR SEQ ID NO:3:

( i ) SEQUENCE CHARACTERISTICS:
( A ) LENGTH: 79 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

TAGCTAGCAG TAACATGGAG CAGTGTTGTT CCGTTAGTTC GTTTATTTG TCGAAATCCG    60

CGACCTGCTC CATGTTACT    79

( 2 ) INFORMATION FOR SEQ ID NO:4:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear (  i  i  ) MOLECULE TYPE: DNA (genomic)

(  x  i  ) SEQUENCE DESCRIPTION: SEQ ID NO:4:

TGTTGTTCCG TTAGTTCGTT TTATT 25

( 2 ) INFORMATION FOR SEQ ID NO:5:

(  i  ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:5:

TCATTGTACC TCGTCCAGCG CCTAAAGCTG TTTATTTTGC TTGATTGCCT TGTTGT 56

( 2 ) INFORMATION FOR SEQ ID NO:6:

(  i  ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:6:

TCATTGTACC TCGTCCAGCG CCTAAAGCTG TTTATTTTGC TTGATTGCCT TGTTGT 56